(12) United States Patent
Trennepohl et al.

(10) Patent No.: US 10,588,786 B2
(45) Date of Patent: Mar. 17, 2020

(54) METHOD AND APPARATUS FOR MICROWAVE PRODUCT TREATMENT

(71) Applicant: The Procter & Gamble Company, Cincinnati, OH (US)

(72) Inventors: Michael Dale Trennepohl, Cincinnati, OH (US); Albert Hill Mandell, Minot, ME (US); Kevin Charles Strong, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 494 days.

(21) Appl. No.: 15/418,032

(22) Filed: Jan. 27, 2017

(65) Prior Publication Data

US 2017/0333259 A1 Nov. 23, 2017

Related U.S. Application Data

(60) Provisional application No. 62/338,776, filed on May 19, 2016.

(51) Int. Cl.
*H05B 6/80* (2006.01)
*F26B 3/347* (2006.01)
*A61F 13/20* (2006.01)

(52) U.S. Cl.
CPC .............................. *A61F 13/2088* (2013.01)

(58) Field of Classification Search
CPC .............................. H05B 6/705; H05B 6/6402
See application file for complete search history.

(56) References Cited

U.S. PATENT DOCUMENTS

| | | | | |
|---|---|---|---|---|
| 3,916,137 A * | 10/1975 | Jurgensen | ................ | H05B 6/78 219/696 |
| 6,297,479 B1 * | 10/2001 | Wefers | ...................... | A23B 7/02 219/388 |
| 6,581,299 B1 * | 6/2003 | Dedieu | ...................... | F26B 7/00 34/259 |
| 8,299,408 B2 * | 10/2012 | Kimrey, Jr. | ............. | F26B 3/347 219/690 |
| 8,501,110 B2 * | 8/2013 | Windsheimer | ............ | A61L 2/04 422/22 |
| 9,380,651 B2 * | 6/2016 | Kimrey, Jr. | ............ | H05B 6/707 |

(Continued)

*Primary Examiner* — Dana Ross
*Assistant Examiner* — Lawrence H Samuels
(74) *Attorney, Agent, or Firm* — C. Brant Cook

(57) ABSTRACT

An apparatus for applying a field of microwave energy for the processing of a material is disclosed. The apparatus comprises an elongate chamber having a longitudinal axis, a first microwave transmitting device radiatingly coupled to the elongate chamber at a first position, and a second microwave transmitting device radiatingly coupled to the elongate chamber at a second position. The first microwave transmitting device is oriented so that a first portion of the microwave energy is directed toward the longitudinal axis. The second microwave transmitting device is disposed so that a second portion of the microwave energy is directed toward the longitudinal axis. The second microwave transmitting device is coupled to the elongate chamber at a position relative to the longitudinal axis that ranges from about 30 degrees to about 150 degrees relative to the position of the first microwave transmitting device relative to the longitudinal axis.

15 Claims, 24 Drawing Sheets

(56) References Cited

U.S. PATENT DOCUMENTS

| | | | |
|---|---|---|---|
| 2004/0104514 A1* | 6/2004 | Ishikawa | B28B 3/206 264/489 |
| 2006/0016805 A1* | 1/2006 | Del Regno | H05B 6/80 219/680 |
| 2007/0079523 A1* | 4/2007 | Kimrey, Jr. | F26B 3/347 34/79 |
| 2007/0194016 A1* | 8/2007 | Dalton | B01J 19/02 219/759 |
| 2008/0110005 A1* | 5/2008 | Gilbert | A61F 13/2085 28/118 |
| 2008/0119811 A1* | 5/2008 | Gilbert | A61F 13/15707 604/385.17 |
| 2009/0032528 A1* | 2/2009 | Risman | H05B 6/74 219/691 |
| 2012/0175364 A1* | 7/2012 | Kimrey, Jr. | H05B 6/707 219/742 |
| 2012/0181267 A1* | 7/2012 | Kimrey, Jr. | H05B 6/701 219/756 |

* cited by examiner

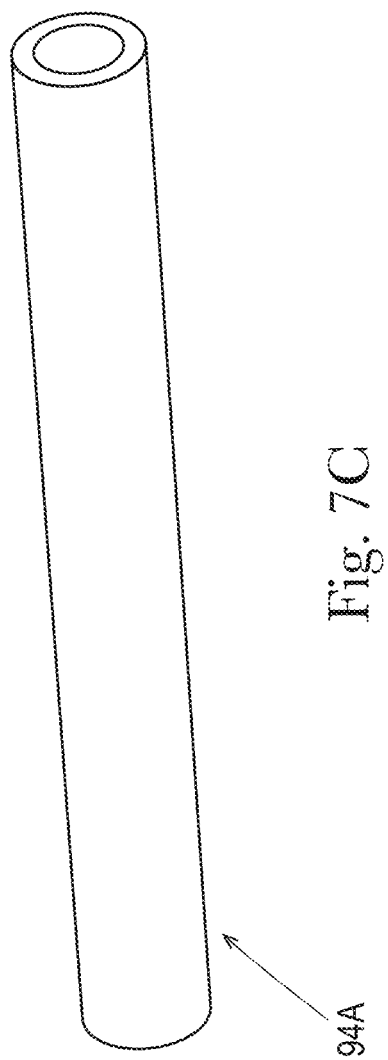

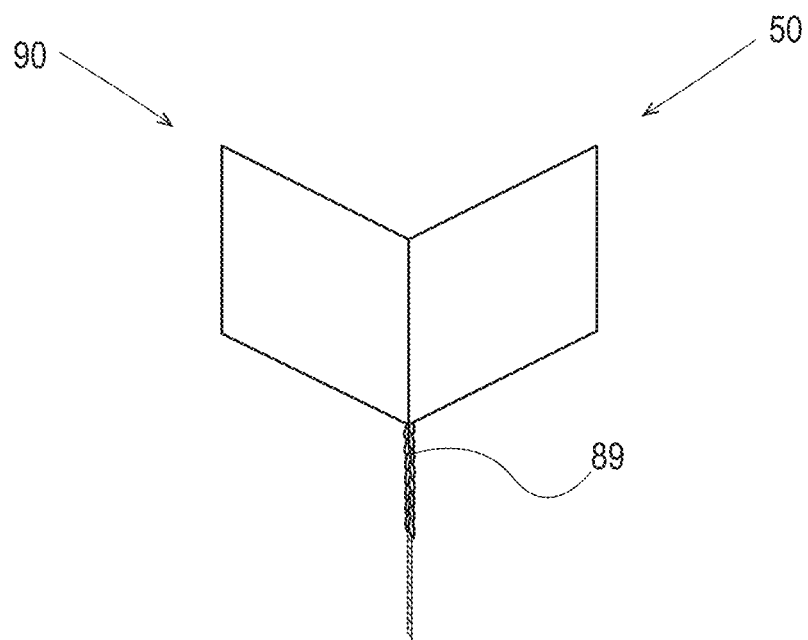
Fig. 8
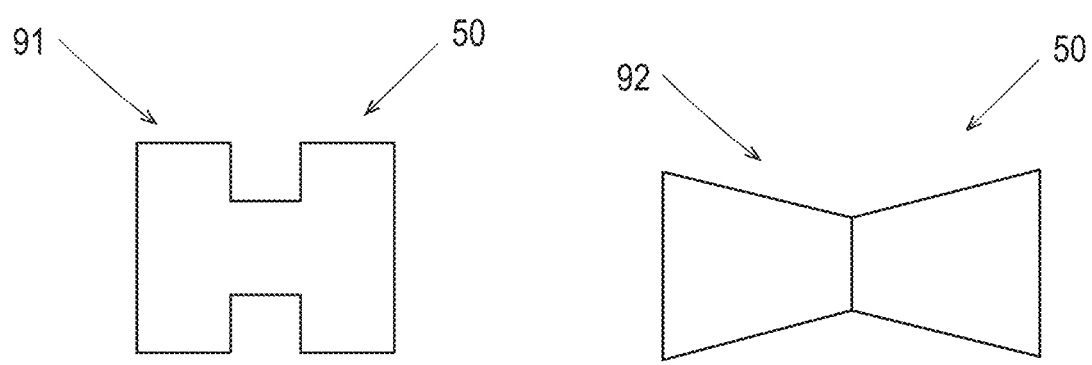
Fig. 9
Fig. 10

METHOD AND APPARATUS FOR MICROWAVE PRODUCT TREATMENT

FIELD OF THE INVENTION

The present disclosure relates to a method and an apparatus for the microwave treatment of materials. The present disclosure more particularly relates to a method and apparatus for the microwave heat-treating production of tampons, other assembled articles, and the like.

BACKGROUND OF THE INVENTION

A wide variety of absorbent catamenial tampons have long been known in the art. Most commercially available tampons are substantially cylindrical in shape prior to use in order to facilitate vaginal insertion. It is well known that the vaginal canal is not smooth and linear, but rather is very contoured. Some digital tampons have tapered insertion ends to make insertion more comfortable. Others have flared withdrawal ends, presumably to provide a larger surface area for the user to push against during insertion. Nevertheless, the inventors of the present invention recognize that comfort and/or ease of the insertion of tampons is an important unmet consumer need. It is also important to have a tampon which is comfortable once inside the contoured vaginal canal. Additionally, it is desirable that the features rendering a tampon comfortable and/or easy to insert do not compromise, and alternatively even enhance the fluid acquisition capabilities of the tampon in use. Therefore, there is a need for new and improved comfortable shaped tampons. The shaped tampon aids in the insertion ease and/or comfort.

During the tampon production process, it is known that after the compression process that affords the tampon with its final shape, the tampon pledget tends to re-expand to its original dimension. To overcome this tendency, heat-setting has been utilized. The application of heat is designed to "set" the tampon in its compressed state. Conventional heat-setting, has some distinct disadvantages. First and foremost of these is the substantial increase in manufacturing time necessary to subject the tampons to an amount of heat necessary to obtain some level of set. If relatively high temperatures are used in an attempt to speed the process, the outside of the tampon which is a dense, compacted material is heated substantially faster than the inside, and the outer surface may be degraded and lose its absorbent characteristics.

Additionally, conductive heating methods typically do not uniformly stabilize the tampon and can result in the alteration of absorbent qualities in the outer layer of the tampon, as the outside of the tampon can dry more quickly than the inside. Conductive heating methods can also be time and energy intensive, as the air within the tampon must be heated, to dry the fibers via conduction from outside the tampon to the inside. Furthermore, high temperatures that could decrease cycle times cannot be utilized in conductive heating methods. The high temperatures may be above the melting point of portions of the tampon, such as the overwrap, which can result in a melted product.

While microwave heating can be a faster method of stabilizing tampons than conductive heating, only a small fraction of the outputted energy used in microwave heating is actually utilized to stabilize the tampon. As a result of this inefficiency, the energy costs of this method are relatively high.

Non uniform electric fields within a microwave oven can cause uneven heating of tampons. The shape of the resonating electric field is a pattern of high and low electric field intensity spots inside the microwaving oven. These spots are caused by standing waves. Standing waves arise due to the interactions that take place between electromagnetic waves bouncing back and forth in the microwaving oven when they are superimposed on one another. The result in this case is a checkered pattern of high and low electric field intensity spots that occurs in the microwaving oven. An exemplary uneven field distribution of microwave energy is shown in FIG. 13). The uneven heating of the tampon results in uneven shape stability of the finished product, an inconsistent consumer experience, and inconsistent product performance.

As such, it would be desirable to provide a method for stabilizing tampons via microwave energy that enables sufficient shape stability without the drawbacks from uneven heating.

SUMMARY OF THE INVENTION

The present disclosure provides for an apparatus for applying a field of microwave energy for the processing of a material. The apparatus comprises an elongate chamber having a proximal end, a distal end, and a longitudinal axis, a first microwave transmitting device radiatingly coupled to the elongate chamber at a first position, and a second microwave transmitting device radiatingly coupled to the elongate chamber at a second position. The elongate chamber has a surface distributed about the longitudinal axis. The proximal end provides ingress for the material into the elongate chamber and the distal end provides egress of the material from the elongate chamber. The first microwave transmitting device is oriented so that a first portion of the microwave energy is transmitted from the first microwave transmitting device and is directed toward the longitudinal axis. The second microwave transmitting device is disposed between the first microwave transmitting device and the distal end and oriented so that a second portion of the microwave energy is transmitted from the second microwave transmitting device and is directed toward the longitudinal axis. The second microwave transmitting device is coupled to the elongate chamber at a position relative to the longitudinal axis that ranges from about 30 degrees to about 150 degrees relative to the position of the first microwave transmitting device relative to the longitudinal axis.

The present disclosure also provides for an apparatus for applying a substantially uniform field of microwave energy for the processing of a material. The apparatus comprises an elongate chamber having a proximal end, a distal end, and a longitudinal axis, a plurality of microwave transmitting devices each radiatingly coupled to the surface of the elongate chamber, a first microwave transmitting device of the plurality of microwave transmitting devices being radiatingly coupled to the surface of the elongate chamber. The elongate chamber has a surface distributed about the longitudinal axis. The proximal end provides ingress for the material into the elongate chamber and the distal end providing egress of the material from the elongate chamber. The first microwave transmitting device being oriented so that a first portion of the microwave energy is transmitted from the first microwave transmitting device is directed toward the longitudinal axis. The second microwave transmitting device being disposed orbitally about the longitudinal axis between the first microwave transmitting device and the distal end. The second microwave transmitting device is oriented so that a second portion of the microwave energy is transmitted from the second microwave transmitting device and is directed toward the longitudinal axis.

BRIEF DESCRIPTION OF THE DRAWINGS

FIG. 7C is a perspective view of an another exemplary tampon carrier mold;

FIG. 8 is a plan view of an exemplary tampon pledget suitable for use with the process and apparatus of the present disclosure;

FIG. 9 is a plan view of another exemplary tampon pledget suitable for use with the process and apparatus of the present disclosure;

FIG. 10 is a plan view of still another exemplary tampon pledget suitable for use with the process and apparatus of the present disclosure;

DETAILED DESCRIPTION

Figure 1:
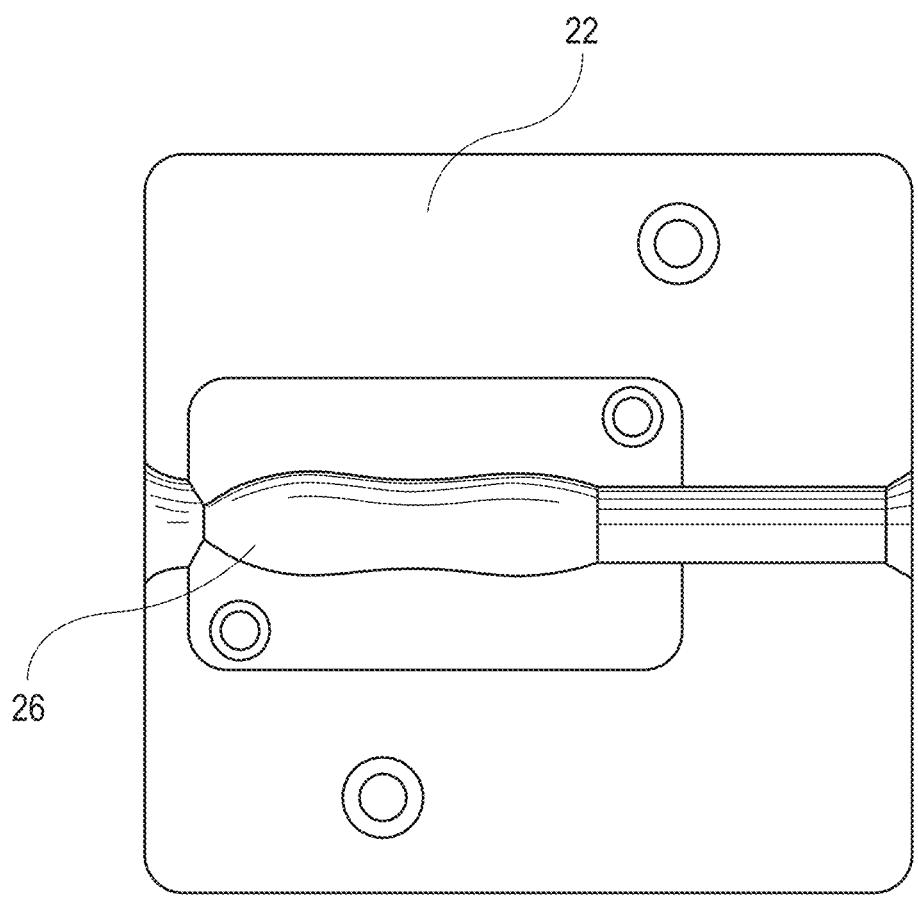
FIG. 1 is a plan view of an exemplary split cavity mold member.

A wide variety of absorbent catamenial tampons have long been known in the art. Most currently commercially available tampons are made from a tampon pledget that has been compressed into a substantially cylindrical form. Prior to compression, the pledget may be rolled, spirally wound, folded, or assembled as a rectangular or laminar pad of absorbent material. The present disclosure provides a new and improved method of stabilizing a tampon. The method has been developed to permit the tampon to be set with minimal impact to expansion properties.

As used herein, the term "tampon" is used to refer to a finished tampon after the compression process referred to below. As used herein the term "tampon" refers to any type of absorbent structure that is inserted into the vaginal canal or other body cavities for the absorption of fluid therefrom. Typically, tampons are constructed from an absorbent material that has been compressed in one or more steps employing one or more parts of the absorbent material in the radial direction, axially along the longitudinal and lateral axes or in both the radial and axial directions to provide a tampon, which is of a size and stability to allow insertion within the vagina or other body cavity. A tampon that has been so compressed is referred to herein as a "self-sustaining" form.

As used herein, "self-sustaining" is a measure of the degree or sufficiency to which the tampon retains the compression applied to the absorbent material of the tampon pledget such that in the subsequent absence of the external forces, the resulting tampon will tend to retain its general shape and size. For example, the resulting tampon's total volume growth subsequent to the removal of the external forces may be no greater than 200% of the external force-restrained shape, preferably less than 150% and even further preferred to not exceed 125% of the external force-restrained shape when observed at ambient room conditions of 73 degrees Fahrenheit temperature and 50% relative humidity. For tampons, it is found that control of the level of moisture within the tampon is a factor for helping the tampon to retain its shape subsequent the absence of the external compression forces. In one embodiment, the tampon is self-sustaining if the level of moisture is about 10% or less. It will be understood by one of skill in the art that this self-sustaining form need not and preferably does not persist during actual use of the tampon. That is, once the tampon is inserted and begins to acquire fluid, the tampon will begin to expand and may lose its self-sustaining form.

As used herein the terms "pledget" or "tampon pledget" are intended to be interchangeable and refer to a construction of absorbent material prior to the compression of such construction into a tampon as described above. Tampon pledgets are sometimes referred to as a tampon blank, or a softwind, or a pad, and the term "pledget" is intended to include such terms as well.

As used herein "compressed" refers to pressing, compacting or squeezing together or to reduce in size or volume as if by squeezing. One method of compaction includes motion of flexible members actuated through air or hydraulics. The tampons herein are typically formed by laterally compacting or rolling the tampon pledget such that the formation processed result in a compressed structure in a vaginally insertable shape.

The term "folded" as used herein, is the configuration of the compressed absorbent member that is incidental or deliberate to compaction of the absorbent material. The folded configuration is characterized by at least one bend at least in a portion of the tampon pledget such that the portion of the tampon pledget is positioned with a different plane than before with the observation that the surface regions near the bend are in a different distal and angular relationship to each other after the folding has taken place. In the case of the lateral compaction of a generally flat tampon pledget, there may exist one or more bends or folds of generally 180 degrees such that the surface regions on either side of the bend may be juxtaposed or even in co-facial contact with each other.

As used herein, "mold" is a structure intended for shaping a compressible or compactable (or fluent) material wherein the structure is so arranged as to define a space or cavity for retaining the compressible material and wherein the compressible material initially having a different form or no definite form conforms to the shape of the space or cavity by the restraining force of the mold structure on the compressible material and preferably changes to a self-sustaining shape even after removal from the mold structure. As defined in this development, the mold cavity or space substantially or fully defines the full surface of the compressed tampon. The mold may have an ingress port or opening wherewith the tampon pledget is introduced into the mold cavity.

As used herein, "holds together" is when two objects are in a close association or relationship with one another and the two objects may be considered a whole.

As used herein, the tampon compression machine is a machine assembly that includes parts that may compress the tampon pledget. Typically a tampon pledget compressed in the tampon compression machine is then transferred to a mold for final shaping into a self-sustaining form of a vaginally insertable shape where often though not required, the mold further compresses parts of the tampon beyond that which the tampon compression machine accomplished prior.

As used herein, the V-Block of the tampon compression machine is used to compress a substantially flat tampon pledget.

As used herein, a transfer member is any member that can used to transfer a compressed tampon pledget.

As used herein, the compression member is any member that can be used to compress a tampon pledget. It can also function optionally as a transfer member.

As used herein, actuating is any force delivered by an electric motor, mechanical transmission, pneumatically, linear drive, manual, and/or hydraulic.

As used herein, a high aspect ratio shape is any shape in which the length is greater than the diameter or width of the shape. The shape may not necessarily contain any defined circles, arcs, or cross-sectional portions.

As used herein, the term "chevron-shaped" is a figure, pattern, or object having the shape of a "V", an inverted "V", broad "U", or an inverted "U."

As used herein, "facing" is to lie near, juxtaposed or in actual contact to another object where any part of a first object is near, juxtaposed or in actual contact with any part of another object.

As used herein, the inner surface of the split cavity mold member is that surface which contacts the material to mold the tampon. The inner surface is shaped or profiled to achieve the desired shape for the tampon. Though not to be limiting, the inner surface of the mold may be any shape as desired.

As used herein, the outer surface of the split half cavity mold is that surface external to the inner surface and can be profiled or shaped in any manner. Often the preferred outer surface shape is dictated by what form or shape is either most convenient to the manufacturer for smooth production and/or least cost.

As used herein, the term "split cavity mold" is a mold comprised of two or more members that when brought together complete the inner surface of the mold, which is intended for shaping a compressible or compactable (or fluent) material wherein the complete mold structure is so arranged as to define a space or cavity. Each member of the mold comprises at least a portion of the inner surface that when brought together or closed completes the mold structure. The split cavity mold is designed such that at least two or more of the mold members can be at least partially separated, if not fully separated, preferably after the tampon has acquired a self-sustaining shape, to expand the cavity volume circumscribed by the inner surface(s) thus permitting the easier removal of the tampon from the mold. Partial separation can occur when only a portion of two mold members are separated while other portions of the two mold members remain in contact. Where each member's inner surface portion joins the inner surface portion of another member, those points of adjacency can define a line, a curve, or another seam of any convoluted intersection or seam of any regular or irregular form. For the purposes of this disclosure, there is at least one complete pathway (regardless of the tortuousness of the path(s)) that travels from along the entire length of the central portion of the tampon, and preferably extends to near the insertion end and/or the insertion tip and/or the withdrawal end (i.e. base or bottom) of a tampon.

The term "split half cavity" indicates a mold that comprises at least two major members. The term "half" indicates one of the two mold members that when brought together complete the mold structure. The term "half" does not necessarily mean that the members are substantially or exactly equivalent to each other in terms of dimensions, shape, volume, weight, etc.

As used herein, an outer sleeve is an optional element. The outer sleeve partially surrounds the mold elements to preferably hold the mold elements in appropriate position relative to each other. The outer sleeve may be a carrying or transport member. The outer sleeve may be constructed from any suitable material including but not limited to tool steel, aluminum, or any form of polymer or resin suitable for a manufacturing environment. In a preferred embodiment, the outer sleeve is comprised of Polybutylene Terephthalate (PBT). While the outer sleeve is commonly generally cylindrical, other shapes such as triangular, semicircular, and rectangular shaped are also acceptable.

As used herein, a joined sleeve cavity mold comprises the outer sleeve and the split cavity mold.

As used herein, a tampon mold comprises a non-compressed or compressed tampon pledget and the split cavity mold.

A "linked split cavity mold member" is a split cavity mold member where at least two of the mold members are physically linked by a linking element or series of linking elements whereas at least one of the linking elements is movable in a linear and/or radial motion to thereby permit the two mold members to be repositioned in space relative to each other while maintaining linkage or connectiveness. The linking element(s) allow the two mold members to be repetitively, for example in a production cycle, be brought or held together (e.g. closed), then separated to the desired degree (e.g. partially opened) then returned to be brought or held together (e.g. closed). The linking elements can be of any form (e.g. bars, rods, linked cams, chains, cables, wires, wedges, screws, etc) and constructed of any material or combination of materials (e.g. tool steel, aluminum, wood, polymers, resins, etc) and actuated by any means including direct force transmission to the linking element(s) or force transmission via one or more of the mold members (or even the finished tampon itself during the opening cycle of the mold).

The term "heat setting" refers to the technique sometimes employed to help the tampon maintain a self-sustaining shape after compression. Heat setting is the introduction of heat energy by one means or another (e.g. thermal temperature gradient conduction, or microwave heating) to cause fiber (inter- or intra-fibrillar) bonding believed due to hydrogen bonding. In the case of microwave heating, the water molecules present in the tampon fibers will disproportionately absorb the microwave energy, transferring heat to the fibers.

"Shaped tampons" refer to tampons having an undercut. The term "undercut" refers to tampons having a protuberance or indentation that impedes the withdrawal from a one piece mold. For example, shaped tampons created by the methods of the present invention may have at least one perimeter in the center of the tampon that is less than both an insertion end perimeter and a withdrawal end perimeter.

An exemplary illustration of the equipment suitable for use, as well as the method of use thereof, for the formation of a shaped tampon is provided in FIGS. 1-12.

A tampon 20 is formed from an absorbent material covered with a nonwoven material, commonly called by those of knowledge in the manufacture of catamenial devices as the overwrap. The resulting material is cut to shape and a removal cord 21 is attached. Once the removal cord 21 is attached, the tampon 20 is compressed into a cylindrical shape. Several devices and accompanying processes exist to form a cylindrically-shaped tampon 20. Exemplary, but non-limiting, devices to form a cylindrically-shaped tampon 20 include a series of converging blades arranged around a circular assembly, a linear slide that acts in a uniaxial fashion, an angled compression jaw, and/or a split cavity mold.

Figure 2:
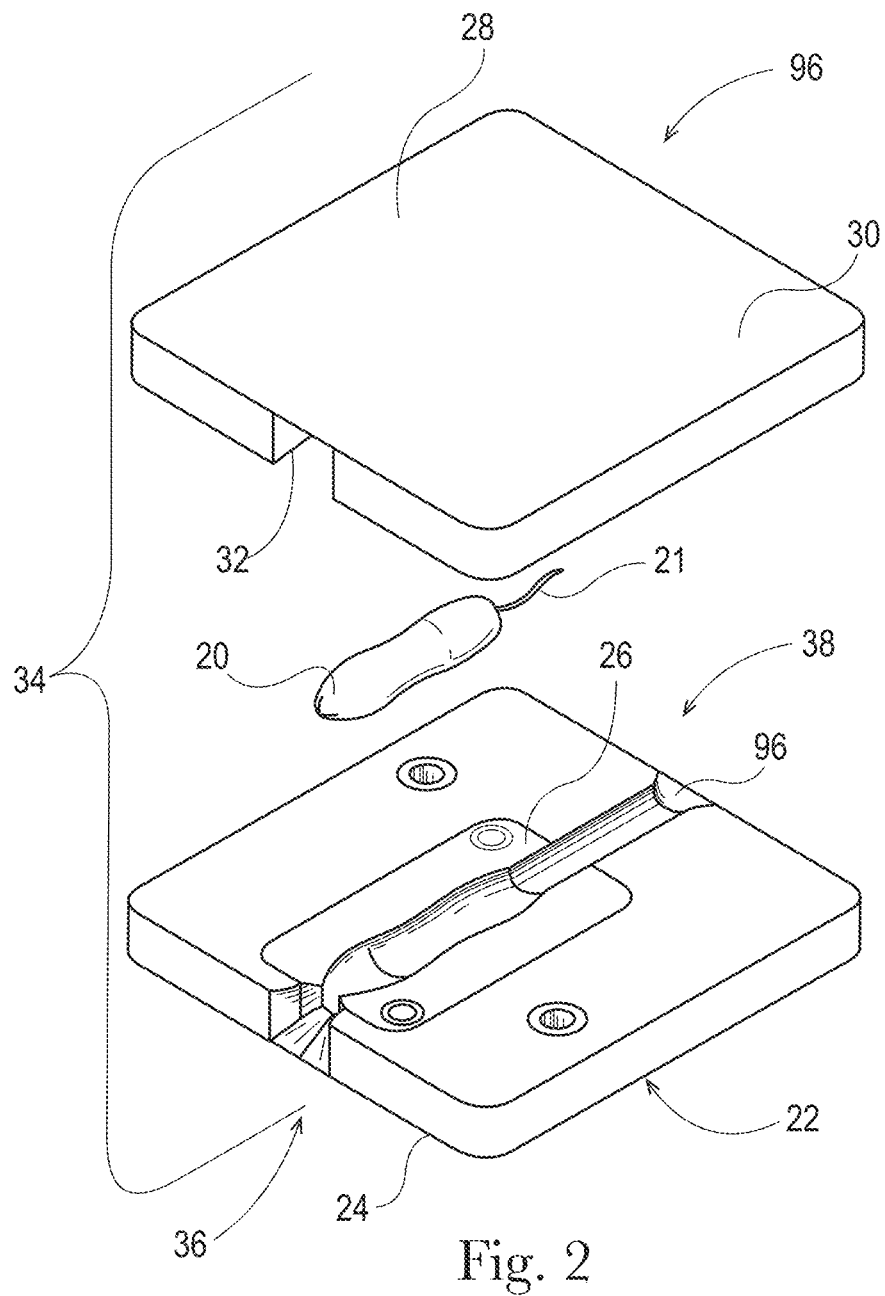
FIG. 2 is an exploded view of an exemplary split cavity mold member.

FIGS. 1-2 respectively provide a plan and perspective view of an exemplary split cavity mold member 22 to form tampon 20. The first split cavity mold member 22 has a first inner surface 26 and a first outer surface 24. A corresponding second split cavity mold member 28 is also provided. The second split cavity mold member 28 is provided with a second inner surface 32 and a second outer surface 30. Depending upon the choice of heat-setting technique, discussed infra, the components of the split cavity mold 34 may be constructed from a wide variety of materials such as an efficaciously microwave transparent material and/or a substantially microwave transparent material.

The first inner surface 26 of the first split cavity mold member 22 can be juxtaposed adjacent to the second inner surface 32 of the second split cavity mold member 28. The combination of the first split cavity mold member 22 and the second split cavity mold member 28 results in a split cavity mold 34. The split cavity mold 34 has a first end 36 and a second end 38. The second end 38 of the split cavity mold 34 has an opening (also referred to herein as ingress port) 96.

Figure 3:
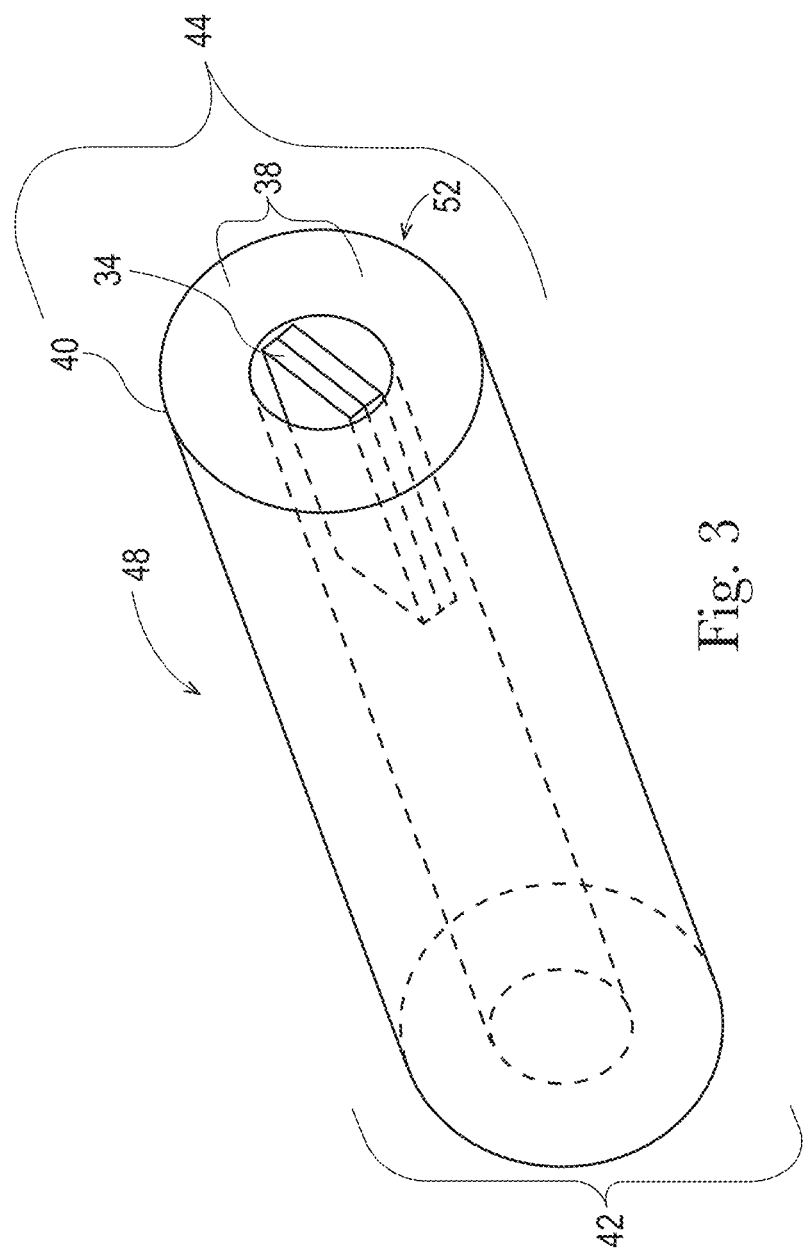
FIG. 3 is a perspective view of an exemplary split cavity mold member placed within an outer sleeve.
Figure 4:
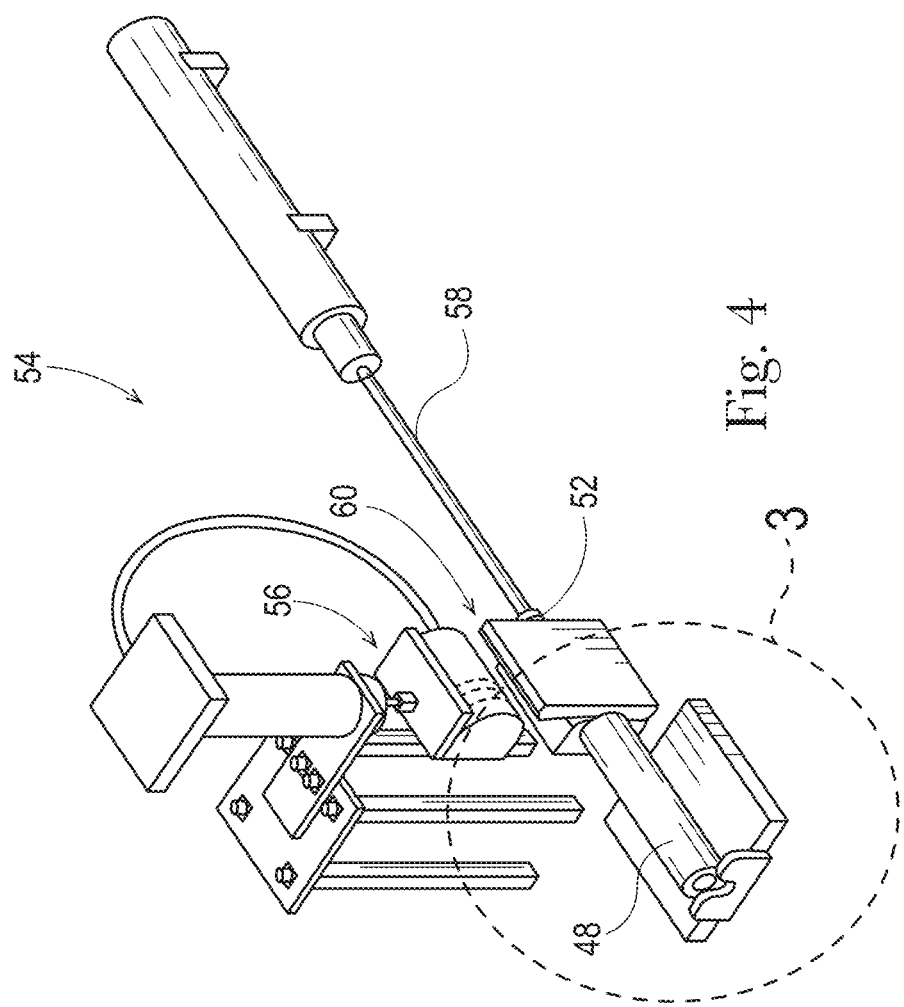
FIG. 4 is a perspective view of an exemplary tampon compression machine suitable for loading a tampon into a split cavity mold member engaged within an outer sleeve.
Figure 5:
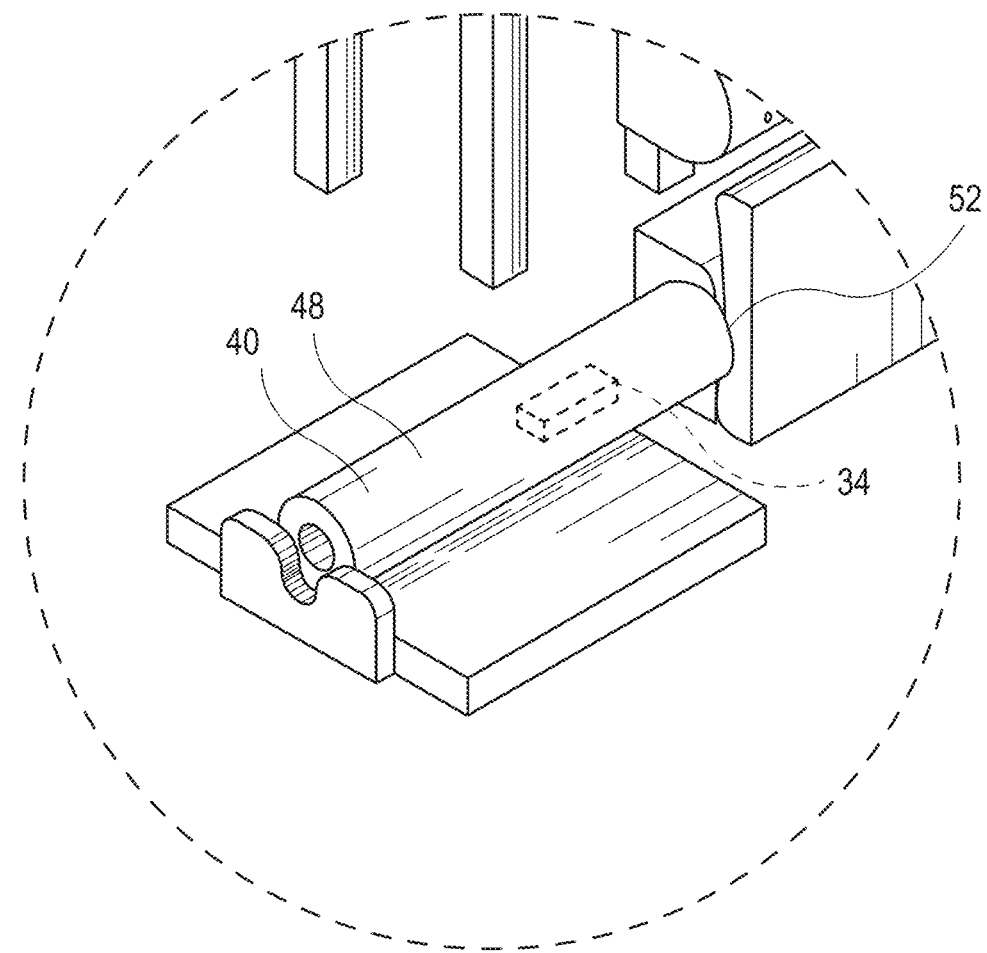
FIG. 5 is an expanded view of the region labeled 3 in FIG. 4.

As shown in FIGS. 3-5, an outer sleeve 40 can be used to join opposing portions of split cavity mold 34. The first end 36 of the split cavity mold 34 may be inserted first into the outer sleeve 40. The opening of the split cavity mold 34 is visible through the second end 44 of the outer sleeve 40. The combination of the split cavity mold 34 and the outer sleeve 40 forms a joined sleeve cavity mold 48 with a transfer end 52. Next, the joined sleeve cavity mold 48 is loaded into a v-block holder 60 of a tampon compression machine 54 with the transfer end 52 of the joined sleeve cavity mold 48 facing a compression jaw 56 in the tampon compression machine 54.

Figure 6A:
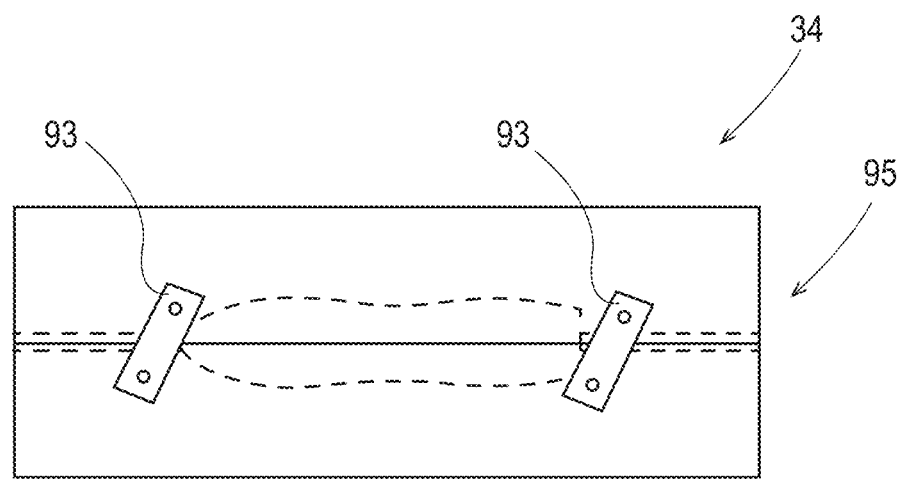
FIG. 6A is a plan view of an exemplary split cavity mold member in a closed position and ready to accept a tampon pledget.
Figure 6B:
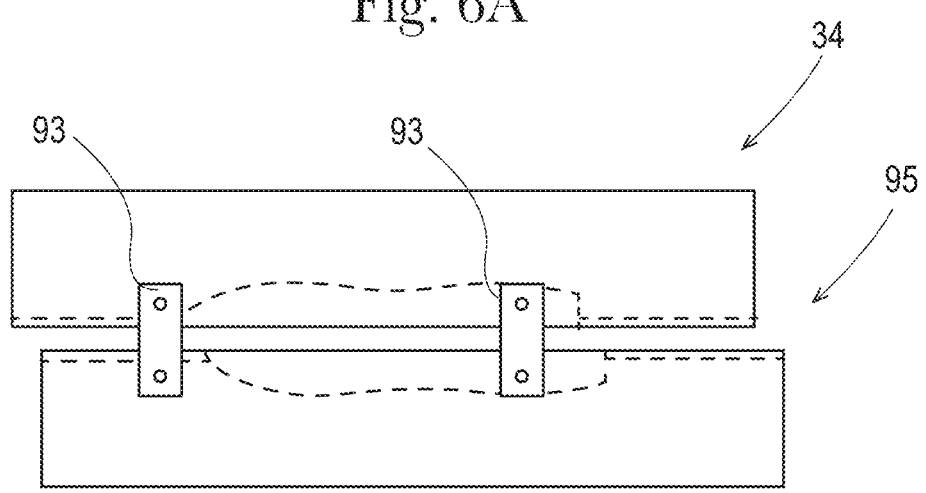
FIG. 6B is a plan view of an exemplary split cavity mold member in an open position suitable for tampon removal.

Alternatively, as shown in FIGS. 6A-6B, a split cavity mold comprising two halves that define a generally concave inner cavity with a generally rectilinear outer surface profile connectable by a linkage system comprising two pairs of pivot arms 93 with a pair on opposite sides of the mold. The pivot arms span across the two length-wise mold member seams. FIG. 6A shows one view of the closed combined mold cavity that is ready to accept a tampon pledget through the opening at end 95 or the ingress port. After the tampon is self-sustaining, the mold is opened manually, mechanically, and/or hydraulically to a degree of separation that allows removal of the tampon from the mold. Opening is accomplished by moving one mold member farther from the other while also shifting it toward one end. In this example, this orients the pivot arms away from the initial inclined position to a more normal direction thereby creating an opening or gap between the two mold members.

As shown in FIG. 6B, as needed the mold can be held open during the tampon removal operation. The mold is then ready to be closed to accept another tampon pledget. When closed, the mold members (whether linked or not) can be locked by any known means including but not limited to interlocking surfaces or tabs as part of the mold itself, third element members that are first attached to the mold members and can lock with each other, etc. The mold separation and closure motion can be accomplished by any known means or drives with external mold elements provided to aid in force transmission as needed, including but not limited to moving arms, screws, wedges, chains, ropes, cams, pistons, lifters, rods, gears, etc.

Figure 7A:
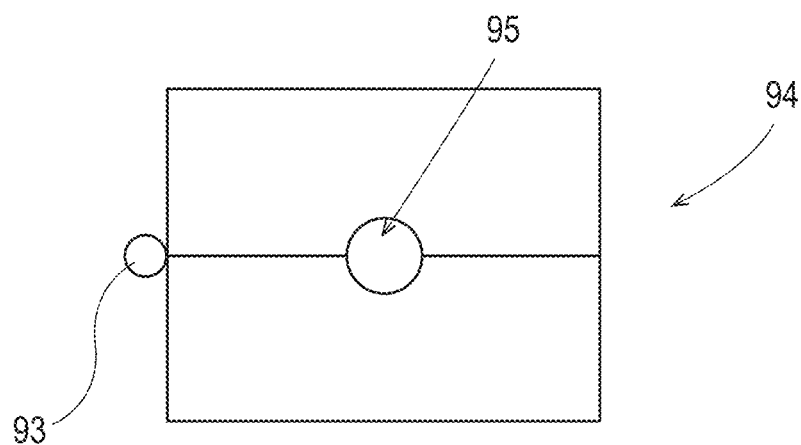
FIG. 7A is a plan view of an alternative embodiment of an exemplary split cavity mold member in a closed position.
Figure 7B:
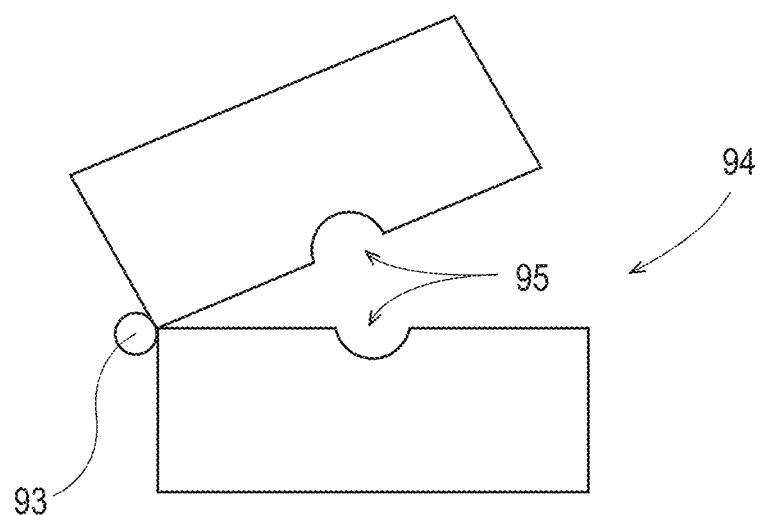
FIG. 7B is a plan view of the exemplary split cavity mold member of FIG. 7A in an open position.
Figure 7D:
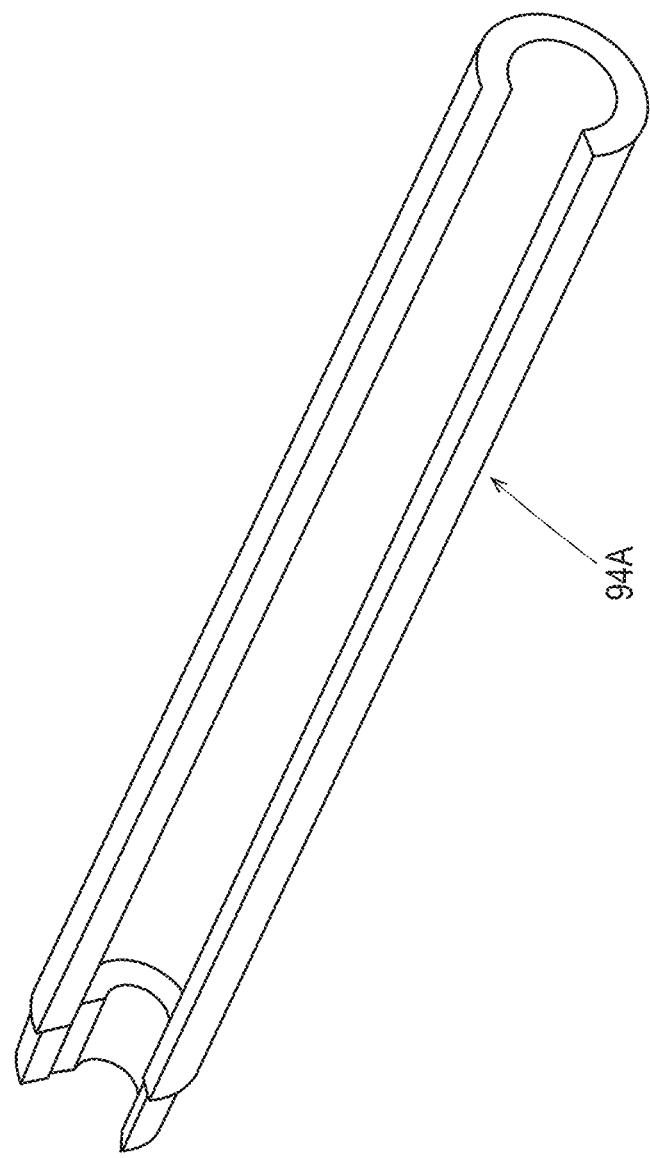
FIG. 7D is a perspective cut-away view of the exemplary tampon carrier mold of FIG. 7C.

Alternatively, as shown in FIGS. 7A and 7B, a split cavity mold 94 can be provided as two halves defining a generally concave inner cavity with a generally rectilinear outer surface profile. Along one of the mold seams is located a long hinge 93, for example a piano-type hinge. FIG. 7A shows two views of the closed combined mold cavity that is ready to accept a tampon pledget through the opening at end 95 or the ingress port.

Referring to FIG. 7B, after the tampon shape is self-sustained, the mold 94 is opened manually, mechanically, and/or hydraulically to a degree of separation that allows removal of the tampon from the mold by pivoting one member away from the other member through the hinge pivot motion. The mold 94 can be held open during the tampon removal operation as required by the manufacturing process. The mold 94 is then ready to be closed to accept another tampon pledget. When closed, the mold members (whether linked or not) can be locked by any known means including but not limited to interlocking surfaces or tabs as part of the mold itself, third element members that are first attached to the mold members and can lock with each other, etc. The mold 94 separation and closure motion can be accomplished by any known means or drives with external mold elements provided to aid in force transmission as needed, including but not limited to moving arms, screws, wedges, chains, ropes, cams, pistons, lifters, rods, gears, etc. As shown in FIGS. 7A-7B, an exemplary carrier mold can be used as a structure for shaping a pledget during compression or retaining the shape of a compressed pledget subsequent to compression, for example during the stabilization process. Carrier molds generally comprise an inner surface defining an inner cavity and an outer surface. The inner cavity is structured to define or mirror the desired shape of the shaped tampon. The inner cavity of a carrier mold may be profiled to achieve any shape known in the art including, but not limited to rectangular, triangular, curved, trapezoidal, semi-circular, hourglass, bottle, serpentine or other suitable shapes. The outer surface of the carrier mold is the surface external to the inner surface and can be profiled or shaped in any manner, such as, rectangular, cylindrical or oblong. The carrier mold may comprise a single integral structure or one or more individual separate component pieces.

The carrier mold of the present disclosure may be used for producing any type of shaped tampon known in the art. Further, the carrier mold of the present disclosure may be used to produce shaped tampons having secondary absorbent members.

A tampon 20 of the present disclosure may be formed from any suitable tampon pledget provided or required by the process, such as tampon pledget 50 shown in FIG. 8. In an alternative embodiment the tampon pledget 50 may have a withdrawal means 89. If the embodiment includes a withdrawal means 89, the withdrawal means 89 is preferably removed out of the path of a jaw movement. The withdrawal means will be joined to the tampon and will be graspable for digital removal after use. The withdrawal means may be joined to any suitable location on the tampon. The withdrawal means may be attached in any suitable manner known in the art including looping, knotting, sewing, adhesive attachment, or a combination of known bonding methods. The withdrawal means may be integral with the absorbent material. Any of the withdrawal means currently known in the art may be used as a suitable withdrawal mechanism. In addition, the withdrawal means can take on other forms such as a ribbon, loop, tab, or the like. The withdrawal means may be a tampon cord.

The tampon pledget 50 portion of the tampon 20 which will be compressed to form the tampon 20 may be any suitable shape, size, material, or construction. In the embodiment shown in FIG. 8, tampon pledget 50 is a batt of absorbent material which is a generally "chevron shaped" pad 90 of absorbent material. While the pledget 50 shown in FIG. 8 can be provided as a generally chevron shape 90, other shapes such as trapezoidal, triangular, semi-circular, and rectangular shaped are also acceptable.

Other shapes that also tend to produce this variation are also possible. For example, the pledget may be generally "H" shaped 91, such as shown in FIG. 9. A "bow tie" shape 92 such as is shown in FIG. 10 is also suitable. While a chevron shaped pledget 50 is suitable, the edges of the chevron may be somewhat "rounded off" in order to facilitate high speed manufacturing operations. As an alternative to the shapes of pledgets described above, a tampon pledget 50 of the present invention may have a uniform shape such as a rectangular shape, but vary in absorbent material density or thickness along the axial extent of the pledget.

The tampon pledget 50, and consequently, the resulting tampon 20 may be constructed from a wide variety of liquid-absorbing materials commonly used in absorbent articles such as rayon, cotton, or comminuted wood pulp which is generally referred to as air felt. Examples of other suitable absorbent materials include creped cellulose wadding; melt-blown polymers including co-form; chemically stiffened, modified or cross-linked cellulosic fibers; synthetic fibers such as crimped polyester fibers; peat moss; foam; tissue including tissue wraps and tissue laminates; or any equivalent material or combinations of materials, or mixtures of these.

Preferred absorbent materials comprise cotton, rayon (including tri-lobal and conventional rayon fibers, and needle punched rayon), folded tissues, woven materials, nonwoven webs, synthetic and/or natural fibers. The tampon 20 and any component thereof may comprise a single material or a combination of materials. Additionally, superabsorbent materials, such as superabsorbent polymers or absorbent gelling materials may be incorporated into the tampon 20.

The tampon pledget 50 and resulting tampon 20 may be formed of a soft absorbent material such as rayon, cotton (including either long fiber cotton or cotton linters) or other suitable natural or synthetic fibers or sheeting. The materials for the tampon 20 can be formed into a fabric, web, or batt that is suitable for use in the tampon pledget 50 by any suitable process such as air-laying, carding, wet-laying, hydro-entangling, or other known techniques.

The pledget may be constructed from a wide variety of liquid-absorbing materials commonly used in absorbent articles. Such materials include but are not limited to rayon (such as GALAXY Rayon (a tri-lobed rayon structure) available as 6140 Rayon; or SARILLE L rayon (a round fiber rayon), both available from Acordis Fibers Ltd., of Hollywall, England), cotton, folded tissues, woven materials, nonwoven webs, synthetic and/or natural fibers or sheeting, comminuted wood pulp which is generally referred to as air-felt, or combinations of these materials. Additionally, superabsorbent materials, such as superabsorbent polymers or absorbent gelling materials may be incorporated into the tampon.

Referring again to FIG. 4, and as discussed generally supra, a tampon pledget 50 is compressed to create a compressed tampon pledget. In an alternative embodiment, the compression can be accomplished by placing the tampon pledget 50 into a compression jaw 56. Next, the compression jaw 56 is actuated. Upon actuating the compression jaw 56, a tampon pledget 50 is compressed into a compressed tampon pledget having a high aspect ratio shape, though other shapes are possible. These may include shapes having a cross section or cross section elements that may be described as rectangular, triangular, trapezoidal, semi-circular, or other suitable shapes. Further, any required compression can be done by any known means in the art.

The compressed tampon pledget 50 can be transferred into the transfer end (or ingress port) of a split cavity mold 34 using a transfer member such as pusher rod which can optionally & preferably be used to axially compress the tampon in the mold. Levers, a multiplicity of small diameter rods radially and axially arranged, or bellows of rubber or other deformable plastic material may also be used as transfer members. Transferring the tampon pledget 50 into the split cavity mold 34 shapes the tampon pledget 50. The compressed tampon pledget 50 and the split cavity mold 34 result in a tampon mold. The tampon mold may have a first end and a second end. The second end of the tampon mold may have an opening. In an alternative embodiment the transfer member is removed. One non-limiting embodiment of the compression members is a compression pusher rod. The compression rod may use a force as appropriate. For example a force of 50-1000 lbf can be suitable. In any regard, it is preferred that the function of transfer and axial compression be distinctly different though a single pusher rod that provides both functions is preferred at pressures and temperatures suitable for compression.

Once in the compressed state, the tampon 20 is typically stabilized (also known as self-sustaining) in a compressed shape. This can be done by applying a high degree of pressure for a period of time, or it can be done via heating. If the tampon 20 is to be shape stabilized via heat, it would be advantageous to transfer the shaped but not yet stable tampon into a carrier that will maintain the tampon's compressed shape. The internal shape of the carrier would be specific to the size and absorbency of the particular tampon 20. Once in the carrier, the tampon 20 may be easily transferred for additional processing.

In certain circumstances, the tampon 20 can become self-sustained under the pressures and constraints of the mold itself; however, it is often desired to add a heat-setting step and to preferably perform a heat-setting step while the tampon is at least partially inside the mold. Heat setting is the introduction of heat energy by one means or another to cause fiber (inter- or intra-fibrillar) bonding believed due to hydrogen bonding. As mentioned supra, any heat-setting step relies on water molecules present within the tampon to disproportionately absorb the applied microwave energy to cause fiber bonding. For heat-setting, control of the internal moisture of the tampon (such as pre-humidifying or pre-drying to certain moisture levels) can be used to control the resulting self-sustaining behavior.

Heat-setting of the tampon 20 can be accomplished by microwaving, thermal conduction, ultrasonic-frequency heating, radio-frequency heating, electromagnetic energy input could be used such as radio waves, and infrared heating with infrared heat transparent molds.

In a preferred embodiment, the pledget 50 and resulting tampon 20 can be stabilized by microwave conditioning during tampon formation. Without wishing to be bound by theory, this step is believed to heat water within the fibers of the pledget 50. This allows greater flexibility in the compression step. For example, if microwave conditioning is used, lower temperatures (such as room temperature or slightly elevated temperatures) during the compression step are sufficient for formation of the final tampon 20. It will be recognized by those of skill in the art that compression to a self sustaining form requires imparting both heat and pressure to the tampon pledget 50. Such heat and pressure causes the fibers to "set" and achieve this self-sustaining form subject to fluid expansion.

Typically, the heat and pressure are provided simultaneously with a heated compression die. This may result in several drawbacks, however. The outer portion of the pledget 50 which contact the surfaces of a compression die may tend to become scorched due to the localized heat. Additionally, the heat imparted by the die may not penetrate into the tampon in a uniform manner. The microwave conditioning overcomes these drawbacks by allowing the pressure to be imparted with a much cooler (for example, room temperature) die. The heat required is imparted by the microwaves which penetrate the tampon 20 more uniformly and which do not tend to scorch the fibers of the tampon 20. This uniform microwave conditioning is also believed to contribute the improved expansion properties associated with the present disclosure.

To be effective, an exemplary tampon carrier mold 94A (shown in FIGS. 7C-7D) is preferably formed from a microwave transparent material or a substantially microwave transparent material in order to prevent the absorption (or minimize the absorption) of microwave energy. This facilitates the process in that the tampon 20 absorbs all of (or at a minimum), a significant portion of the available microwave energy. The absorption of microwaves by the tampon 20 may be enhanced by the presence of any water in the tampon 20 absorbent material. One of skill in the art will appreciate that water will tend to absorb more microwave energy than typical absorbent fibers, and will rapidly conduct the heat into the tampon absorbent fibers. In this way, the tampon 20 can be heated to a desired temperature using microwave energy with the shape defined by the carrier mold 94, 94A that contains the tampon 20. Once the tampon 20 has been heated sufficiently and the shape is stable, the tampon 20 can be removed from the carrier and processed further for delivery to the consumer.

Since each of the carriers 94, 94A are preferably not absorbent (invisible) relative to microwave energy, each carrier 94, 94A can pass through the microwave process with little concern. Thus, it is preferred that each of the carriers 94, 94A be conveyed through a suitable microwave process in a manner that is compatible with, and has a minimal impact on, the electromagnetic field. By way of example, one of skill in the art will recognize that it would be preferable to utilize a conveyance system (e.g., a conveyor) made from a material that has a low microwave absorption property and structural elements that also have a low microwave absorption property. One exemplary material for the conveyor belt would be woven Teflon belting. An exemplary material for the structural elements would be a non-metallic compound, potentially polymeric in nature. One such material is Rexolite, available from C-Lec Plastics, Inc.

It was surprisingly found that the addition of metallic cation salts to a tampon 20 or pledget 50, for example by adding metallic cation salts to liquids, such as water to wet or moisten the absorbent material of a tampon 20 or pledget 50, or metallic cation salts added during tampon 20 or pledget 50 processing, can substantially reduce the time usually required to condition the absorbent material when the absorbent material is heated by microwave radiation. Such increased conditioning speed can increase the output of tampons 20 produced, which can, for example, reduce processing and energy costs.

An exemplary, but non-limiting, microwaving self-sustaining method provides for the split cavity mold 34 to be placed in a microwaving unit where the split cavity mold 34 and an outer sleeve 40 (if used) are made from a microwave transparent material(s).

Figure 11:
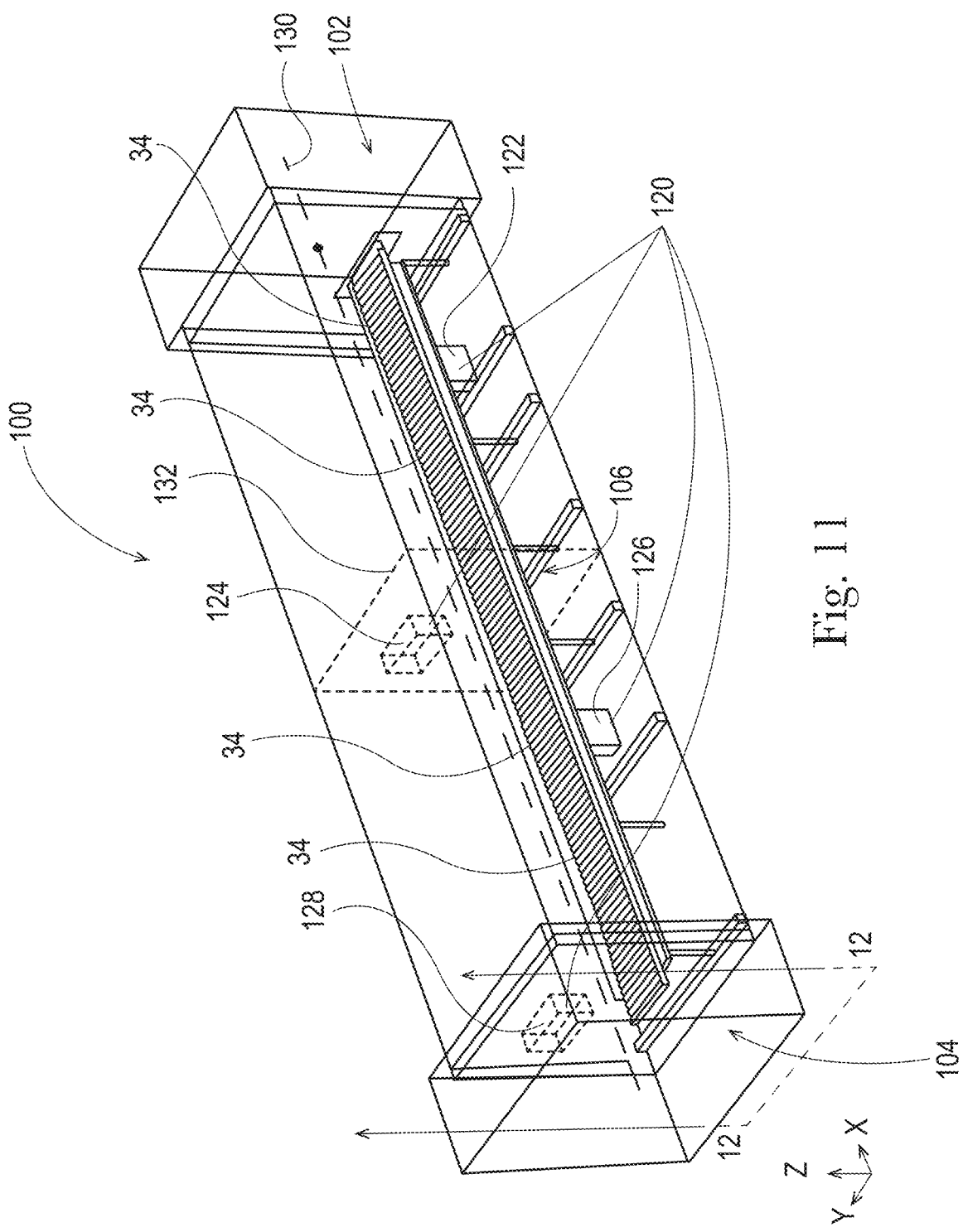
FIG. 11 is a perspective view of an exemplary continuous feed elongate microwave oven suitable for producing tampons consistent with the current disclosure.
Figure 12:
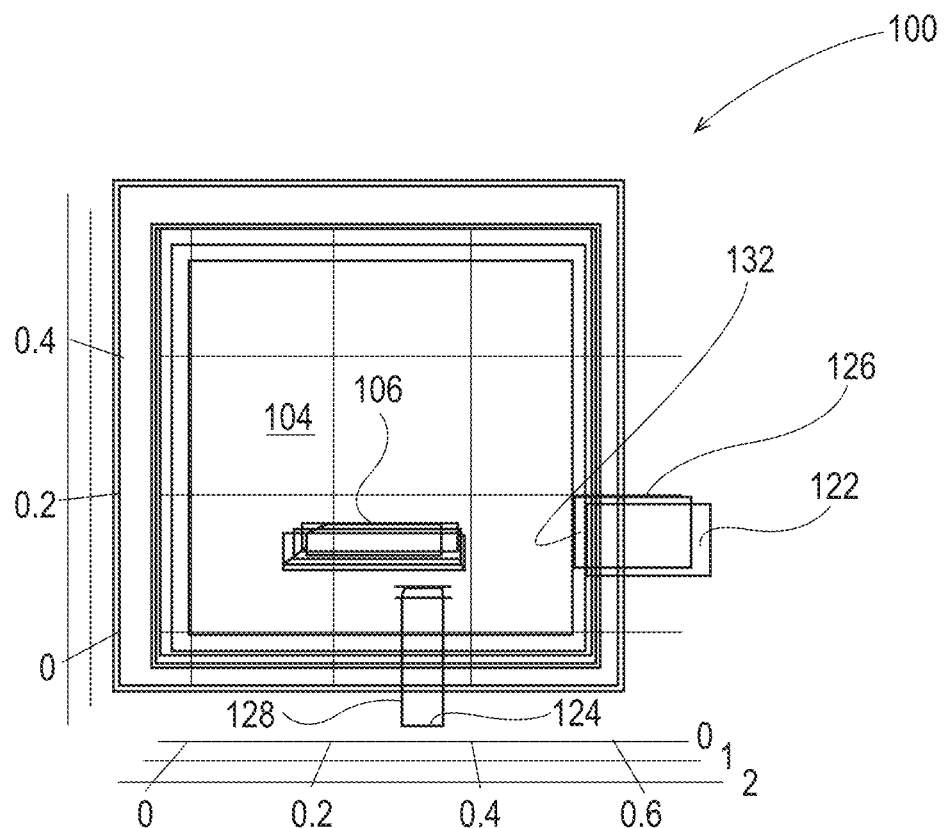
FIG. 12 is a cross-sectional view of the exemplary continuous feed elongate microwave oven suitable for producing tampons of FIG. 12 taken along the lines 12-12.

Referring to FIGS. 11 and 12, a continuous feed elongate microwaving oven is shown generally at 100. The oven includes an entrance end 102 and an exit end 104. A conveyor system 106 (here shown as a continuous conveyor belt), is driven through the continuous feed elongate microwaving oven 100 between the entrance end 102 and exit end 104. Preferably, the conveyor belt 106 is constructed from microwave transparent material, and/or a substantially microwave transparent material. The conveyor belt 106 is constructed to provide cooperative engagement between the conveyor belt 106 with at least one respective split cavity mold 34 and/or outer sleeve 40. A respective split cavity mold 34 and/or outer sleeve 40 is brought into contacting and removable engagement with a portion of conveyor belt 106 at the entrance end 102 of continuous feed elongate microwaving oven 100 and is removed from contacting engagement with conveyor belt 106 at the exit end 104 of continuous feed elongate microwaving oven 100.

The respective split cavity mold 34 and/or outer sleeve 40 to be cured are conveyed through the continuous feed elongate microwaving oven 100 by the conveyor belt 106. The conveyor belt 106 may be driven by a conventional motor drive unit (not shown), as is well known in the art, to convey the respective split cavity mold 34 and/or outer sleeve 40 serially past a series of microwave emitters (or microwave transmitting devices) 120 (e.g., first microwave transmitting device 122, second microwave transmitting device 124, third microwave transmitting device 126, fourth microwave transmitting device 128, and so on . . . ). Preferably chokes (not shown) are arranged at the entrance end 102 and exit end 104 to inhibit microwave leakage from the continuous feed elongate microwaving oven 100. Further, any door included in the oven 100, preferably includes a quarter wave choke to further prevent microwave leakage from the continuous feed elongate microwaving oven 100.

Arranged orbitally about the longitudinal axis 130, and radiatingly coupled, to the continuous feed elongate microwaving oven 100 are a series of microwave transmitting devices 120 (e.g., first microwave transmitting device 122, second microwave transmitting device 124, third microwave transmitting device 126, fourth microwave transmitting device 128, and so on . . . ). The series of microwave transmitting devices 120 are disposed between entrance end (or proximal end) 102 and exit end (or distal end) 104 of the continuous feed elongate microwaving oven 100. In a preferred embodiment, each respective microwave transmitting device of the series of microwave transmitting devices 120 can be arranged from about 4 to about 8 inches from the longitudinal axis 130 and is radiatingly coupled to the continuous feed elongate microwaving oven 100 and directs microwave energy toward conveyor belt 106 and/or longitudinal axis 130.

In one embodiment of the present disclosure, first microwave transmitting device 122 is disposed at a first position proximate to, or adjacent to, entrance end 102 of continuous feed elongate microwaving oven 100 so that first microwave transmitting device 122 is radiatingly coupled to the continuous feed elongate microwaving oven 100 so that microwave energy emitted from the first microwave transmitting device 122 is directed into the continuous feed elongate microwaving oven 100 and toward the longitudinal axis 130 and/or conveyor belt 106 of continuous feed elongate microwaving oven 100. Preferably, second microwave transmitting device 124 is disposed at a second position between first microwave transmitting device 122 and the distal end 104 of continuous feed elongate microwaving oven 100. Further, second microwave transmitting device 124 is preferably radiatingly coupled to the continuous feed elongate microwaving oven 100 so that microwave energy emitted from the second microwave transmitting device 124 is directed into the continuous feed elongate microwaving oven 100 and toward the longitudinal axis 130 and/or conveyor belt 106 of continuous feed elongate microwaving oven 100.

In one embodiment, the first microwave transmitting device 122 and the second microwave transmitting device 124 are radiatingly coupled to the continuous feed elongate microwaving oven 100 so that the second microwave transmitting device 124 at a position relative to longitudinal axis 130 that ranges from at least about 30 degrees to about 150 degrees relative to the position of the first microwave transmitting device 122 relative to the longitudinal axis 130. In another embodiment, the first microwave transmitting device 122 and the second microwave transmitting device 124 are radiatingly coupled to the continuous feed elongate microwaving oven 100 so that the second microwave transmitting device 124 at a position relative to longitudinal axis 130 that ranges from at least about 45 degrees to about 120 degrees relative to the position of the first microwave transmitting device 122 relative to the longitudinal axis 130. In yet another embodiment, the first microwave transmitting device 122 and the second microwave transmitting device 124 are radiatingly coupled to the continuous feed elongate microwaving oven 100 so that the second microwave transmitting device 124 at a position relative to longitudinal axis 130 that ranges from at least about 60 degrees to about 100 degrees relative to the position of the first microwave transmitting device 122 relative to the longitudinal axis 130. In yet a further embodiment, the first microwave transmitting device 122 and the second microwave transmitting device 124 are radiatingly coupled to the continuous feed elongate microwaving oven 100 so that the second microwave transmitting device 124 at a position relative to longitudinal axis 130 that is 90 degrees relative to the position of the first microwave transmitting device 122 relative to the longitudinal axis 130.

In one embodiment of the present disclosure, a third microwave transmitting device 126 is disposed at a third position between second microwave transmitting device 124 and the distal end 104 of continuous feed elongate microwaving oven 100. Further, the third microwave transmitting device 126 is preferably radiatingly coupled to the continuous feed elongate microwaving oven 100 so that microwave energy emitted from the third microwave transmitting device 126 is directed into the continuous feed elongate microwaving oven 100 and toward the longitudinal axis 130 and/or conveyor belt 106 of continuous feed elongate microwaving oven 100. Additionally, one of skill in the art could provide a fourth microwave transmitting device 128 is disposed at a fourth position between the third microwave transmitting device 126 and the distal end 104 of continuous feed elongate microwaving oven 100. Further, the fourth microwave transmitting device 128 is preferably radiatingly coupled to the continuous feed elongate microwaving oven 100 so that microwave energy emitted from the fourth microwave transmitting device 128 is directed into the continuous feed elongate microwaving oven 100 and toward the longitudinal axis 130 and/or conveyor belt 106 of continuous feed elongate microwaving oven 100. One of skill in the art could provide any number of microwave transmitting devices as may be required by the system or manufacturing process.

It can be preferable to provide the microwave transmitting devices comprising the series of microwave transmitting devices 120 as being radiatingly coupled to continuous feed elongate microwaving oven 100 in an orthogonal, alternating fashion about the longitudinal axis 130 and/or conveyor belt 106 of continuous feed elongate microwaving oven 100. By way of non-limiting example, and as shown in FIGS. 11-12, if first microwave transmitting device 122 is disposed at a first radial position relative to the longitudinal axis 130 and/or conveyor belt 106 of continuous feed elongate microwaving oven 100, the second microwave transmitting device 124 could be disposed orthogonal to the first microwave transmitting device 122 relative to the longitudinal axis 130 and/or conveyor belt 106 of continuous feed elongate microwaving oven 100. In other words, if the first microwave transmitting device 122 is disposed at the 6 o'clock position, the second microwave transmitting device 124 could be disposed at the 3 o'clock position. Similarly, the third microwave transmitting device 126 could be disposed orthogonally to the second microwave transmitting device 124 relative to the longitudinal axis 130 and/or conveyor belt 106 of continuous feed elongate microwaving oven 100 (i.e., in-line with first microwave transmitting device 122). Further, the fourth microwave transmitting device 128 could be disposed relative to the longitudinal axis 130 and/or conveyor belt 106 of continuous feed elongate microwaving oven 100 (e.g., in-line with second microwave transmitting device 124). However, one of skill in the art would easily recognize that each respective microwave transmitting device of the series of microwave transmitting devices 120 can have any radiatingly coupled arrangement about the longitudinal axis 130 and/or conveyor belt 106 of continuous feed elongate microwaving oven 100.

One of skill in the art will understand the efficacy of providing a choke at the openings into the continuous feed elongate microwaving oven 100 for the prevention of microwave energy escape from continuous feed elongate microwaving oven 100. In practice a choke can reflect a portion of any applied microwave energy back into the chamber and absorb any energy not immediately reflected back. There are numerous designs for microwave chokes, and most are designed for the specific frequency of microwave energy.

Microwave radiation can be applied at any suitable power level. Depending on the physical properties of tampon pledget 50, tampon 20, split cavity mold 34, and/or outer sleeve 40, the total emitted microwave energy can be in the range of about 1 kilowatts (kW) to about 24 kW. Suitable power levels include, for example, at least about 1 kW, at least about 1.5 kW, at least about 2 kW, at least about 2.5 kW, at least about 3 kW, at least about 3.5 kW, at least about 4 kW, at least about 4.5 kW, at least about 5 kW, at least about 5.5 kW, at least about 6 kW, at least about 6.5 kW, at least about 7 kW, at least about 7.5 kW, at least about 8 kW, at least about 8.5 kW, at least about 9 kW, or more. Microwave radiation can be supplied in a suitable manner, such as by using a machine capable of generating microwaves. Microwave energy is supplied to microwave transmitting device can be provided by a microwave generator such as Cober Model S6F, available from Cober Electronics, Inc., Stamford, Conn.

Preferably, the tampon pledget 50 and/or tampon 20 of the present invention are subject to conditioning a microwave source for about 18 seconds±about 5 seconds or for about 10 seconds. Junior absorbency tampons may be subject to this microwave source at a power level of about 4.2 kW or about 3 kW. Regular absorbency tampons are preferably subject to microwaves at a power level of about 6 kW or about 5 kW. Super absorbency tampons are preferably subject to microwaves at a power level of about 8 kW or about 7 kW. Super Plus absorbency tampons are preferably subject to microwaves at a power level of about 9 kW or about 8.5 kW.

The microwave energy from each microwave transmitting device is directed into the tampon pledget 50 and/or tampon 20. The application of microwave energy results in the rapid oscillation of the molecules in the tampon pledget 50 and/or tampon 20 that cause the requisite heating and conditioning. In a preferred embodiment, each microwave transmitting device of the series of microwave transmitting devices 120 emits an equal portion of the total amount of microwave energy that is applied to the tampon pledget 50 and/or tampon 20. In another embodiment, each microwave transmitting device of the series of microwave transmitting devices 120 emits a defined portion of the total amount of microwave energy that is applied to the tampon pledget 50 and/or tampon 20. For example, first microwave transmitting device 122 can emit about 45 percent of the total amount of microwave energy that is applied to the tampon pledget 50 and/or tampon 20. Correspondingly, second microwave transmitting device 124 can emit about 35 percent of the total amount of microwave energy that is applied to the tampon pledget 50 and/or tampon 20. Third microwave transmitting device 126 can emit about 20 percent of the total amount of microwave energy that is applied to the tampon pledget 50 and/or tampon 20. Fourth microwave transmitting device 128 can emit about 0 percent of the total amount of microwave energy that is applied to the tampon pledget 50 and/or tampon 20. Naturally, one of skill in the art would be able to provide each respective microwave transmitting device of the series of microwave transmitting devices 120 with any portion of the total amount of microwave energy that is to be applied to the tampon pledget 50 and/or tampon 20. In this way, each tampon pledget 50 and/or tampon 20 can be exposed to a defined, or desired, microwave energy profile that is required in order to provide the tampon pledget 50 and/or tampon 20 with the desired microwave conditioning. The specific tailoring of the energy profile can enable the most efficient processing of numerous different size and shape tampons on one manufacturing process.

In any manner in which microwave energy is provided into continuous feed elongate microwaving oven 100, it is preferred that the microwave energy be provided in a field that is substantially uniformly distributed about tampon pledget 50 and/or tampon 20.

As seen in FIGS. 13-24, the applied electric field within a given microwave oven can be parsed into groups based on the strength of the field and plotted as iso-surfaces. One of skill in the art will understand that the ideal field would be one with the most consistent levels of electric field—that is a solid block of iso-surface. The more variation that is present in the electric field, the more the iso-surfaces will be separated and have gaps between them. For consistency, the scale on all plots is set to the same electric field values and the total power input is the same.

Figure 13:
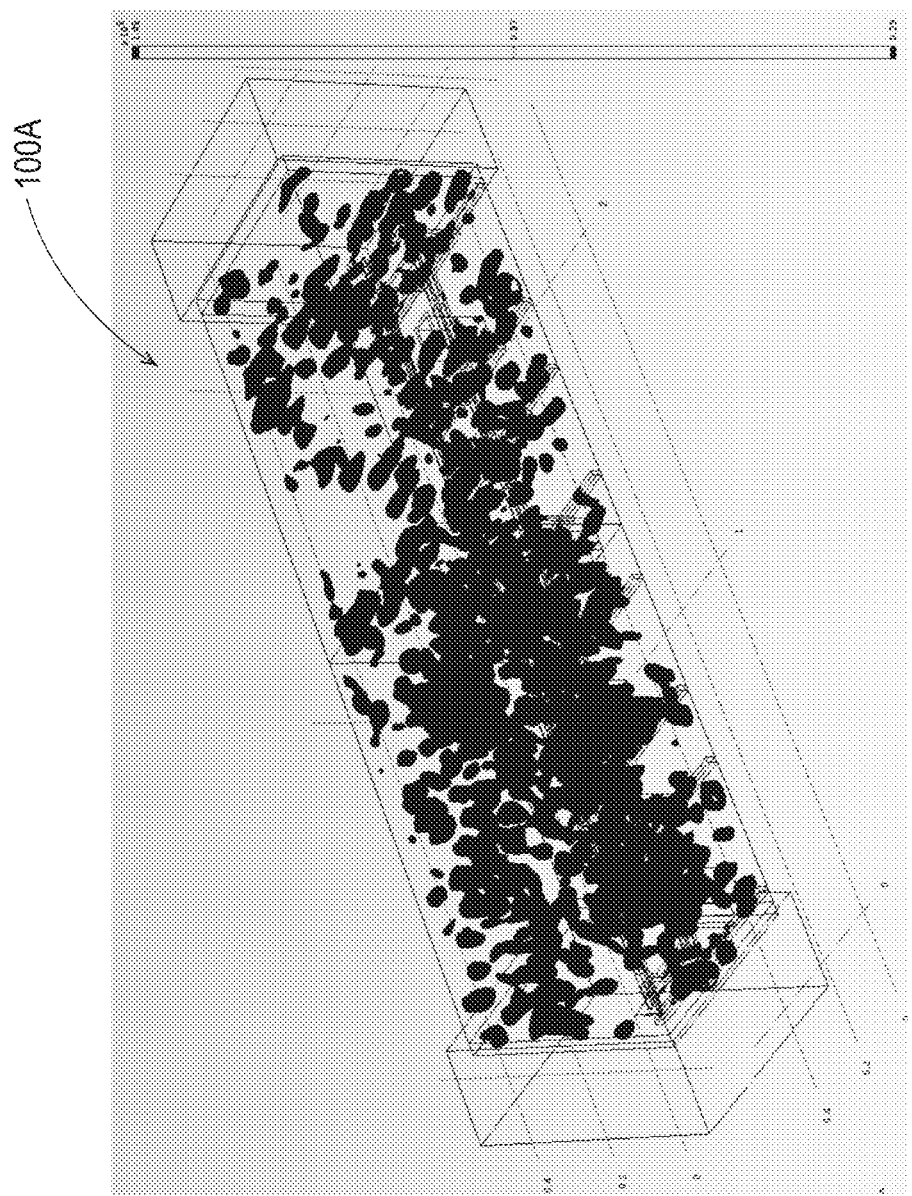
FIG. 13 is an exemplary E-field radiation density iso-surface plot of an exemplary prior art elongate microwave oven.
Figure 14:
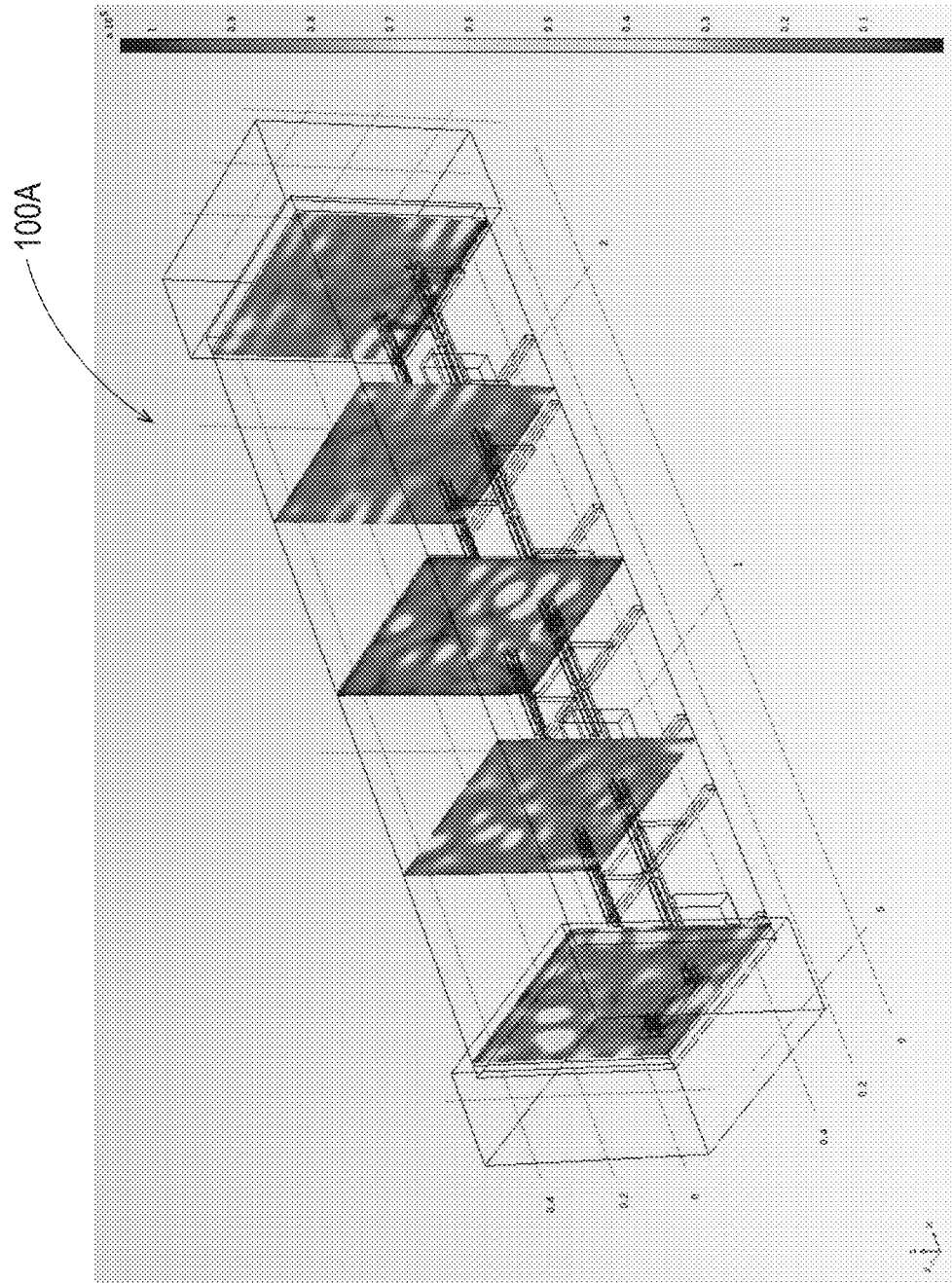
FIG. 14 is a plurality of cross-sectional views of an exemplary E-field radiation density plot in a plane formed by the y-z axis of the exemplary prior art elongate microwave oven of FIG. 13.
Figure 15:
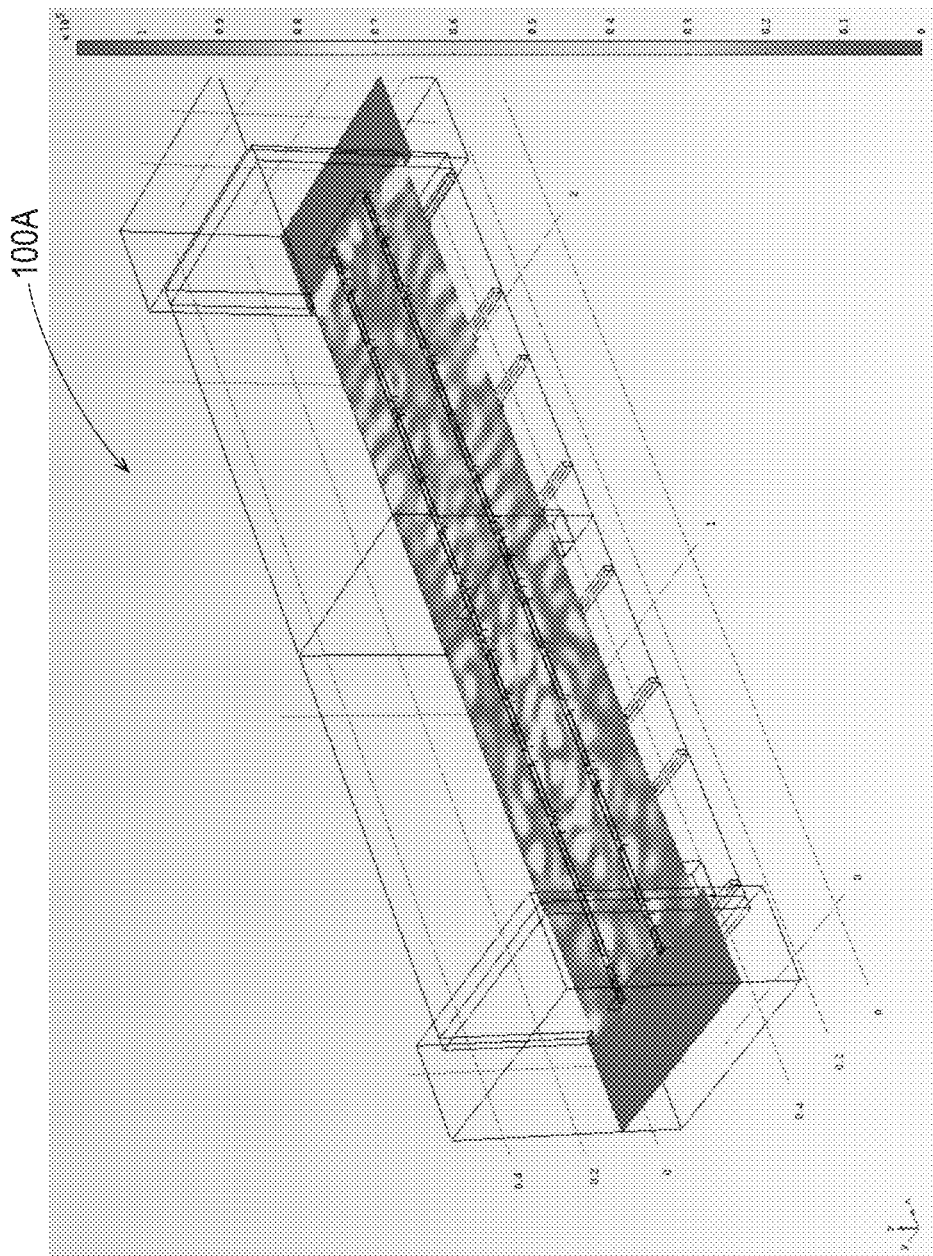
FIG. 15 is a cross-sectional view of an exemplary E-field radiation density plot in a plane formed by the x-y axis of the exemplary prior art elongate microwave oven of FIG. 13.

It was found that prior art executions that provided a series of microwave transmitters that were distributed in a collectively linear manner about the horizontal axis of a microwaving oven provided a microwave energy field that is significantly non-uniform. As shown in FIGS. 13-15, an exemplary distribution of e-field energy within a prior art microwaving oven using such collectively linear placement of a series of microwave transmitters (i.e., all microwave transmitters are disposed upon one side of the microwave oven) has significant numbers of microwave "hot spots." In other words, the E-field strength is non-uniformly distributed throughout the interior volume of the microwaving oven. This non-uniform distribution of microwave energy can be shown through the use of a color map that identifies the microwave energy hot spots as well as depict the uniformity of such microwave energy distribution (known to those of skill in the art as a field distribution). In other words, the microwave energy disposed into the interior volume of the microwave oven by the linearly aligned microwave transmitters lying within an identified range of desired E-field strengths (e.g., ranging from between about $0.29\times10^5$ $V/m^2$ and $1.45\times10^5$ $V/m^2$) can be graphically represented and analyzed for field uniformity/non-uniformity within the microwave oven.

Such analysis can include a review of the overall E-field uniformity (FIG. 13) where the non-colored regions represent an E-field distribution outside the desired E-field limits. Further, a review of the y-z cross-sectional E-field distribution (FIG. 14) identifies several hot-spots (shown by lighter/brighter color representations). A review of the x-y cross-sectional E-field distribution (FIG. 15) also shows the presence of a non-uniform E-field density in the plane of the tampon pledget 50 and/or tampon 20 as it passes through the microwave oven 100A. In short, a review of the various E-field density plots for a prior art series of microwave transmitters distributed in a collectively linear manner about the horizontal axis of a microwaving oven shows a substantial non-uniformity in the desired E-field density and the presence of several hot spots. In other words, there is a scattered E-field density.

Figure 16:
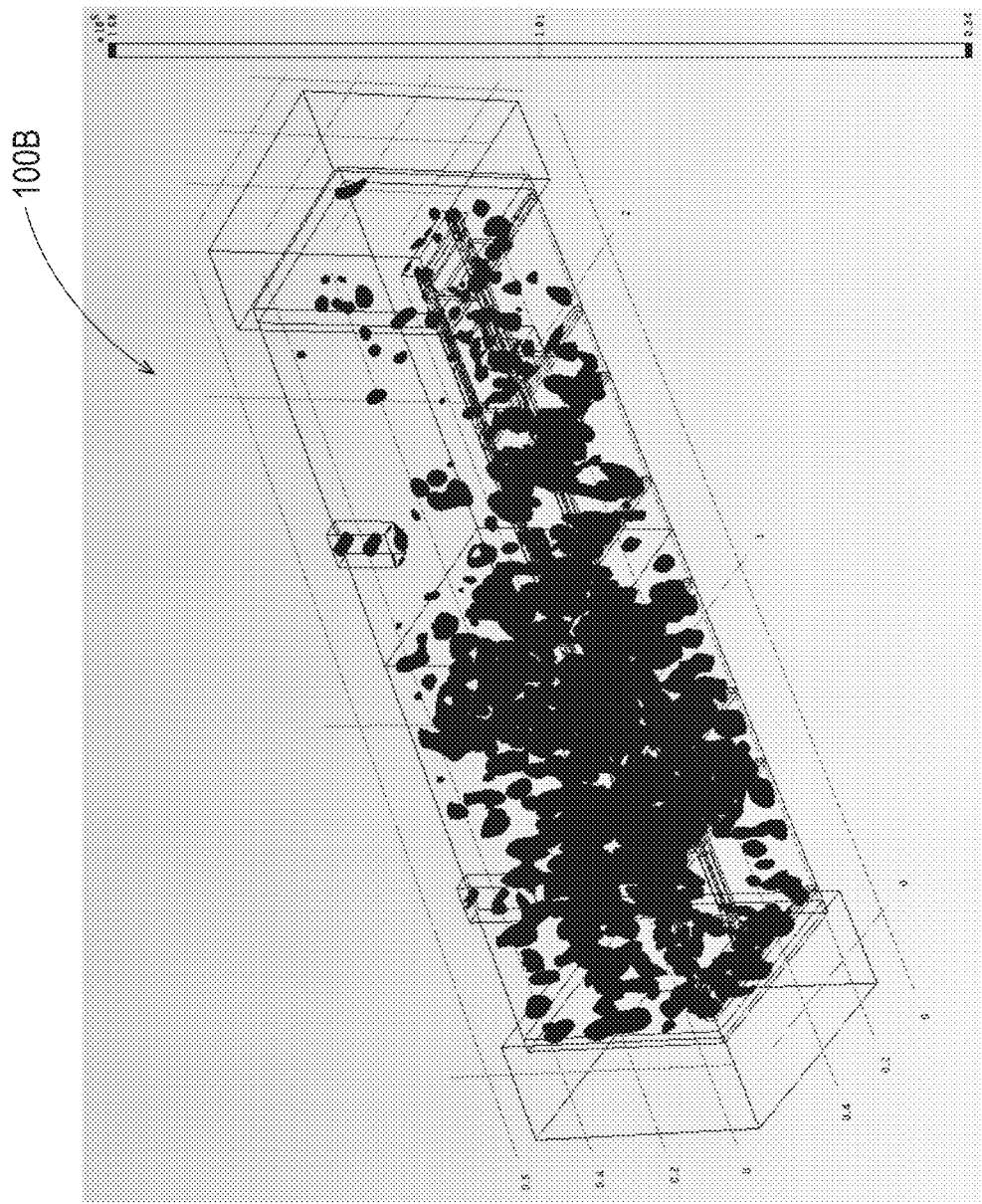
FIG. 16 is an exemplary E-field radiation density iso-surface plot of another exemplary prior art elongate microwave oven.
Figure 17:
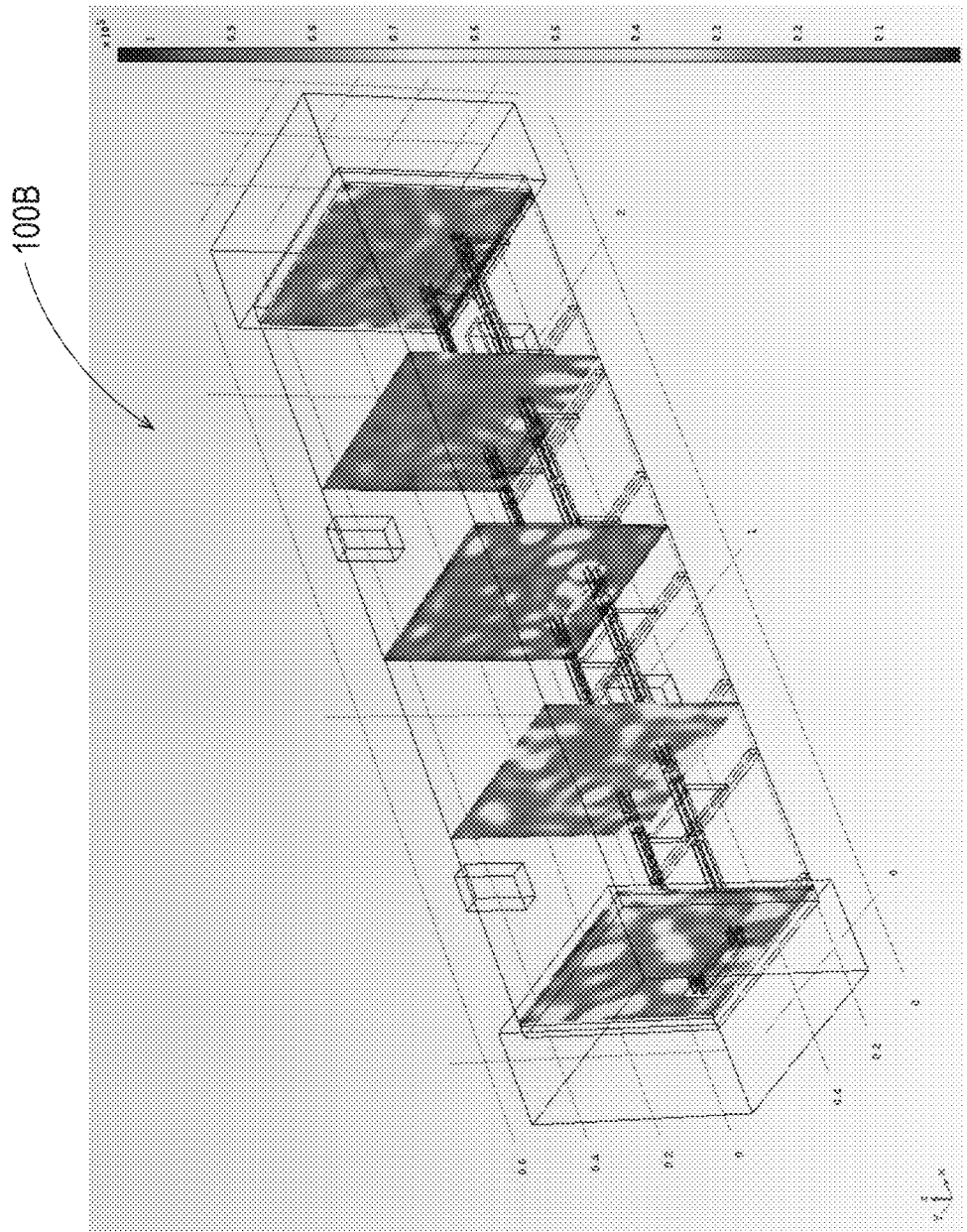
FIG. 17 is a plurality of cross-sectional views of an exemplary E-field radiation density plot in a plane formed by the y-z axis of the exemplary prior art elongate microwave oven of FIG. 16.
Figure 18:
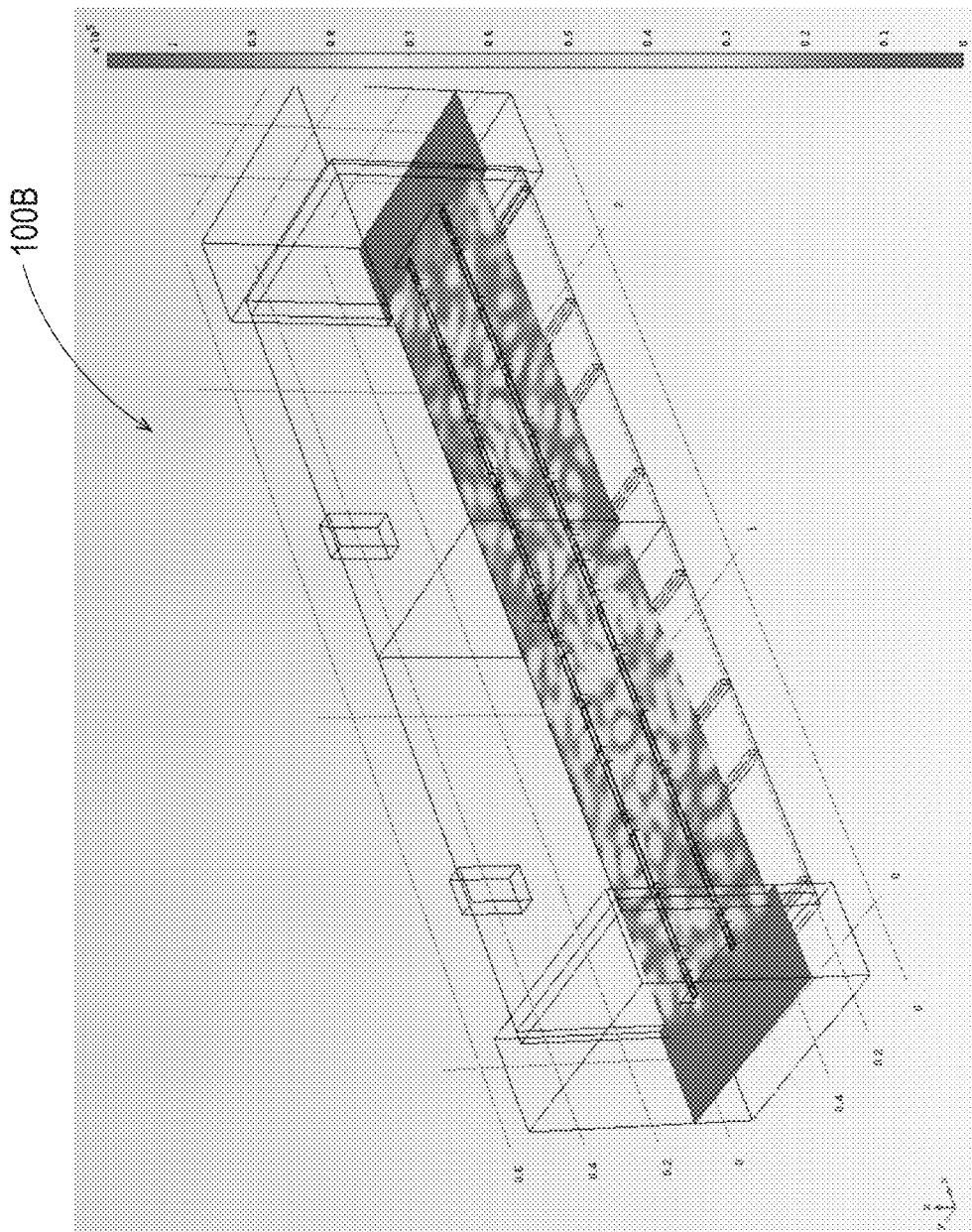
FIG. 18 is a cross-sectional view of an exemplary E-field radiation density plot in a plane formed by the x-y axis of the exemplary prior art elongate microwave oven of FIG. 16.

As shown in FIGS. 16-18, in an alternative prior art placement of microwave transmitters about a microwave oven in a co-planar, alternating manner (e.g., a first transmitter disposed below the articles, the next above the articles, etc.) provides even more clear indications of non-uniform E-field density applied to the tampon pledget 50 and/or tampon 20 as it passes through the microwave oven 100B. For example, the non-colored regions of FIG. 16 represent an E-field distribution outside the desired E-field limits inside the first chamber of prior art microwave oven 100B. Further, a review of the y-z cross-sectional E-field distribution (FIG. 17) identifies numerous hot-spots (shown by lighter/brighter color representations). A review of the x-y cross-sectional E-field distribution (FIG. 18) also shows the presence of a non-uniform E-field density in the plane of the tampon pledget 50 and/or tampon 20 as it passes through the microwave oven 100B. In short, a review of the various E-field density plots for a prior art series of microwave transmitters distributed in a linear, co-planar, but opposing linear manner about the horizontal axis of a microwaving oven shows a substantial non-uniformity in the desired E-field density and the presence of several hot spots. In other words, providing a planar, alternating magnetron orientation, provides a lot of open area in the right portion of the microwave cavity, indicating a field that is not very uniform in that part of the cavity.

Figure 19:
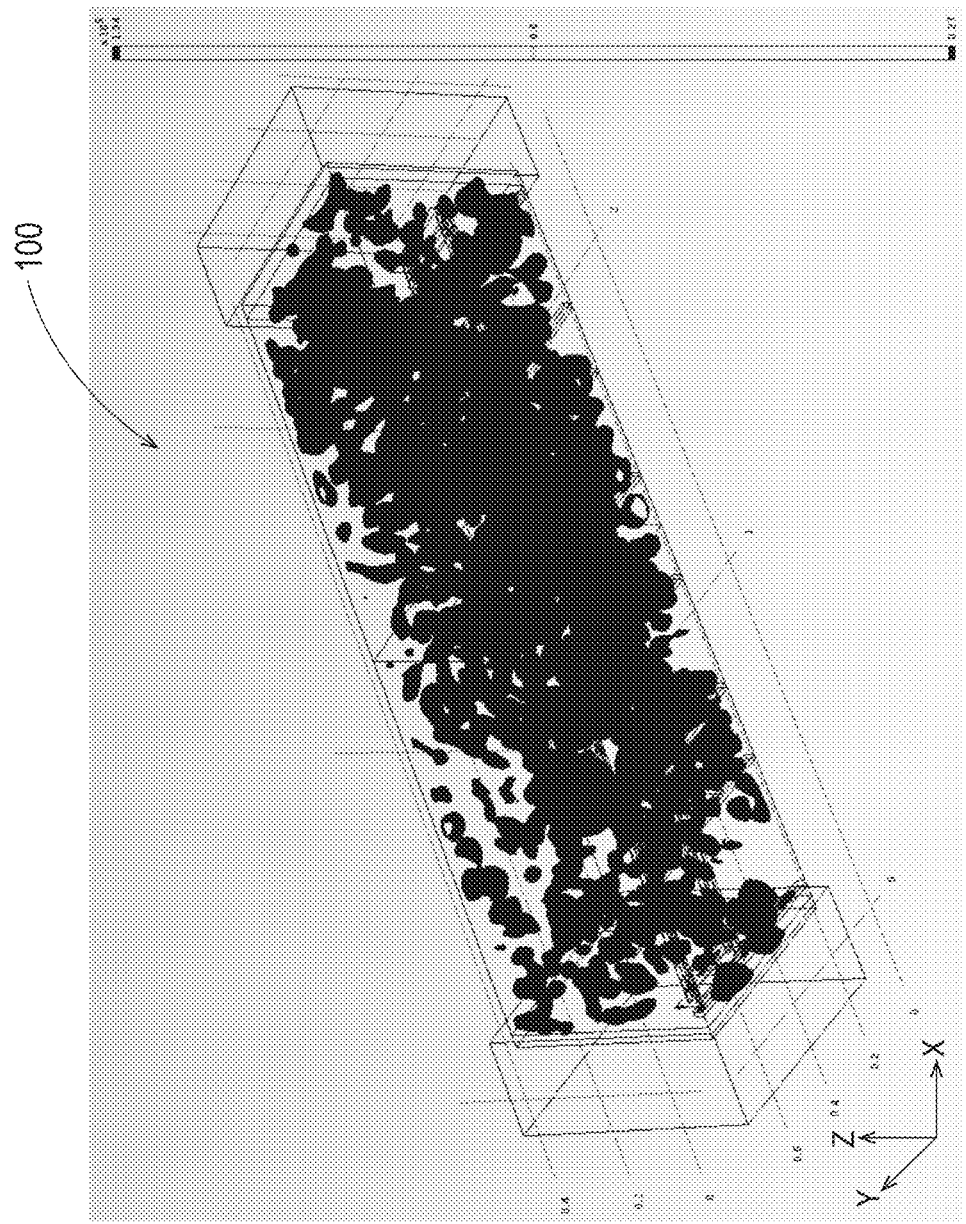
FIG. 19 is an exemplary E-field radiation density iso-surface plot of an exemplary elongate microwave oven having microwave transmitters disposed about the longitudinal axis of the elongate microwave oven and in an alternating orthogonal relationship relative to each other and where each microwave transmitter provides a nearly identical microwave output as described herein.
Figure 20:
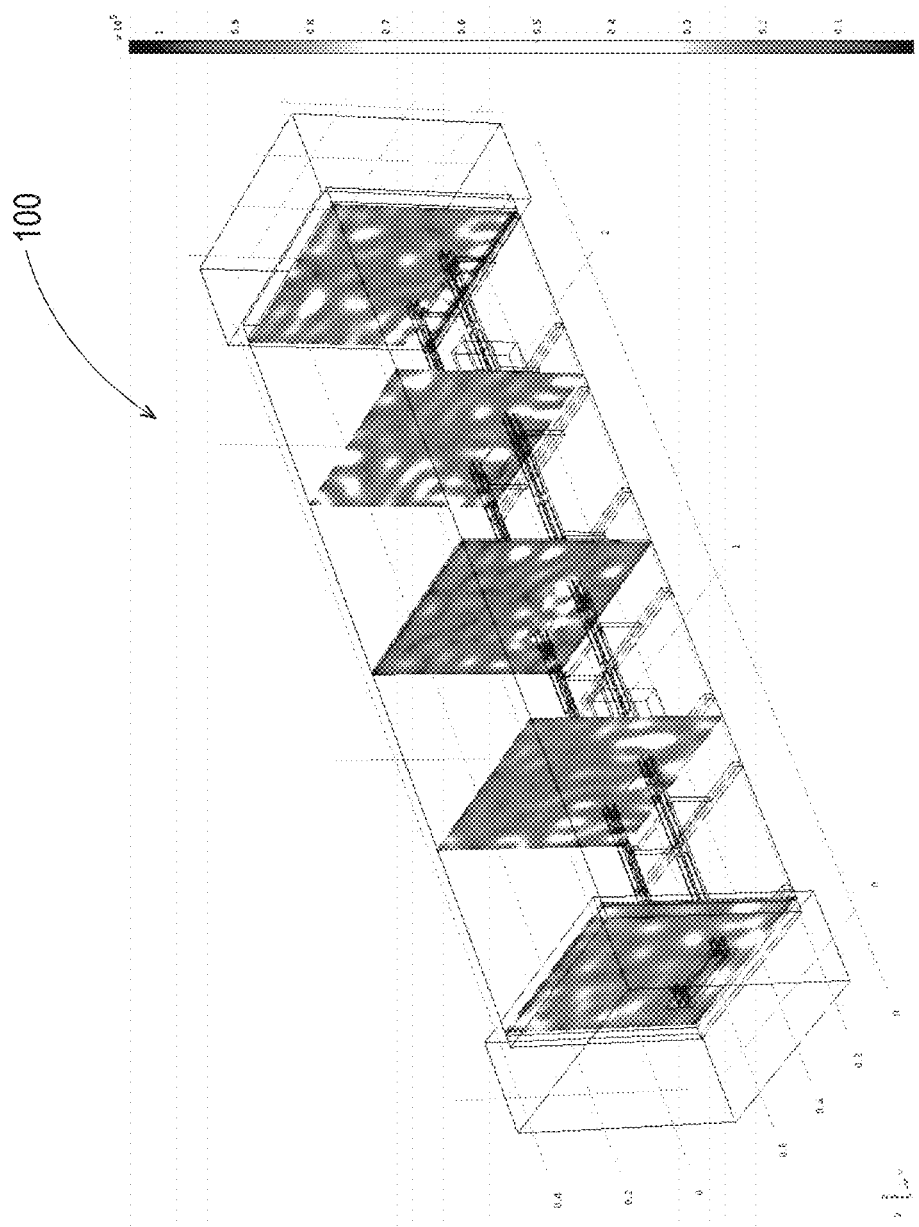
FIG. 20 is a plurality of cross-sectional views of an exemplary E-field radiation density plot in a plane formed by the y-z axis of the exemplary elongate microwave oven of FIG. 19.
Figure 21:
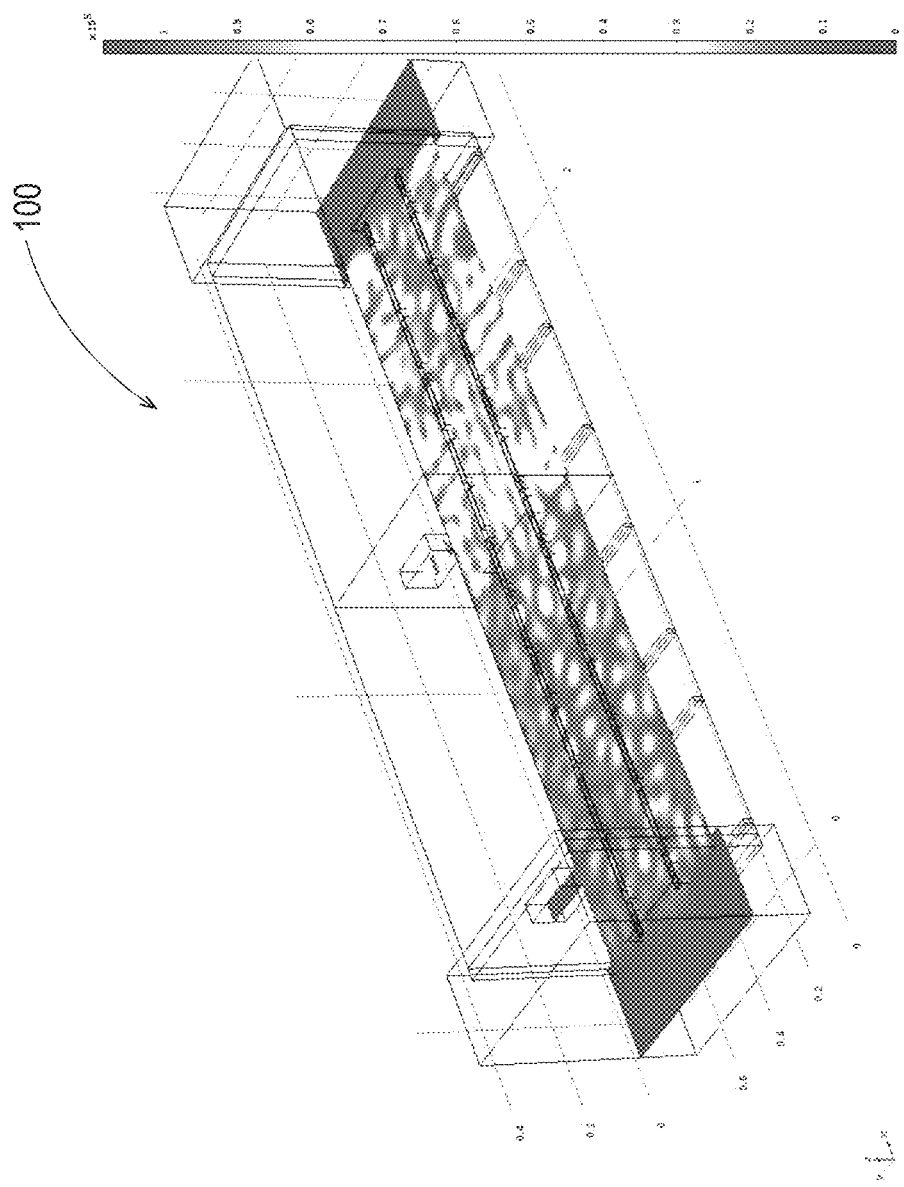
FIG. 21 is a cross-sectional view of an exemplary E-field radiation density plot in a plane formed by the x-y axis of the exemplary elongate microwave oven of FIG. 19.

Contrastingly, the placement of microwave transmitters about a microwave oven in an alternating manner (e.g., a first transmitter disposed below the articles, the next alongside the articles, etc.) as described supra, provides clear indications of a substantially uniform E-field density applied to the tampon pledget 50 and/or tampon 20 as it passes through the microwave oven 100. In other words, to arrive at an EM field that is the most homogeneous, it was found that utilizing a 90-degree relationship between adjacent magnetrons was provided a substantially homogenous E-field. As shown in FIG. 19, the evidence indicates a marked decrease in the presence of non-colored regions representing an E-field distribution substantially inside the desired E-field limits inside both the first and second chambers of continuous feed elongate microwaving oven 100. Further, a review of the y-z cross-sectional E-field distribution (FIG. 20) does not identify any hot-spots (as would be shown by lighter/brighter color representations). A review of the x-y cross-sectional E-field distribution (FIG. 21) also shows the presence of a substantially uniform E-field density in the plane of the tampon pledget 50 and/or tampon 20 as it passes through the continuous feed elongate microwaving oven 100. In short, a review of the various E-field density plots for a series of microwave transmitters distributed about continuous feed elongate microwaving oven 100 as described supra shows substantial uniformity in the desired E-field density and the absence of hot spots.

When configuring the magnetrons of the continuous feed elongate microwaving oven 100 in a 90 degree orthogonal configuration (e.g., bottom wall and back wall as described supra), a much more consistent presence of the iso-surfaces is observed. This indicates a higher degree of uniformity in the electric field present within the continuous feed elongate microwaving oven 100. A higher uniformity of electric field can result in more consistent heating rates, fewer hotspots within continuous feed elongate microwaving oven 100 that could result in fires or damage, and a more consistent product quality.

Without desiring to be bound by theory, it is believed that the model of the E-field density within continuous feed elongate microwaving oven 100 as described supra has focused on coupling the solution of the Maxwell equation with the heat transfer components of the conditioning process. That is, one solves the electromagnetic field and uses it to determine the amount of heat generated in the tampons at different positions within the continuous feed elongate microwaving oven 100 along the path the tampons would travel from the inlet to the outlet. While a direct simulation may not be possible, an iterative approach can be taken that approximates the direct simulation. It can be preferred to focus on the orthogonal positions of the magnetrons about the longitudinal axis of continuous feed elongate microwaving oven 100 and their orthogonal orientation, the size of the inlet and outlets to continuous feed elongate microwaving oven 100, and the power scheme (i.e., how much power each magnetron provides).

Figure 22:
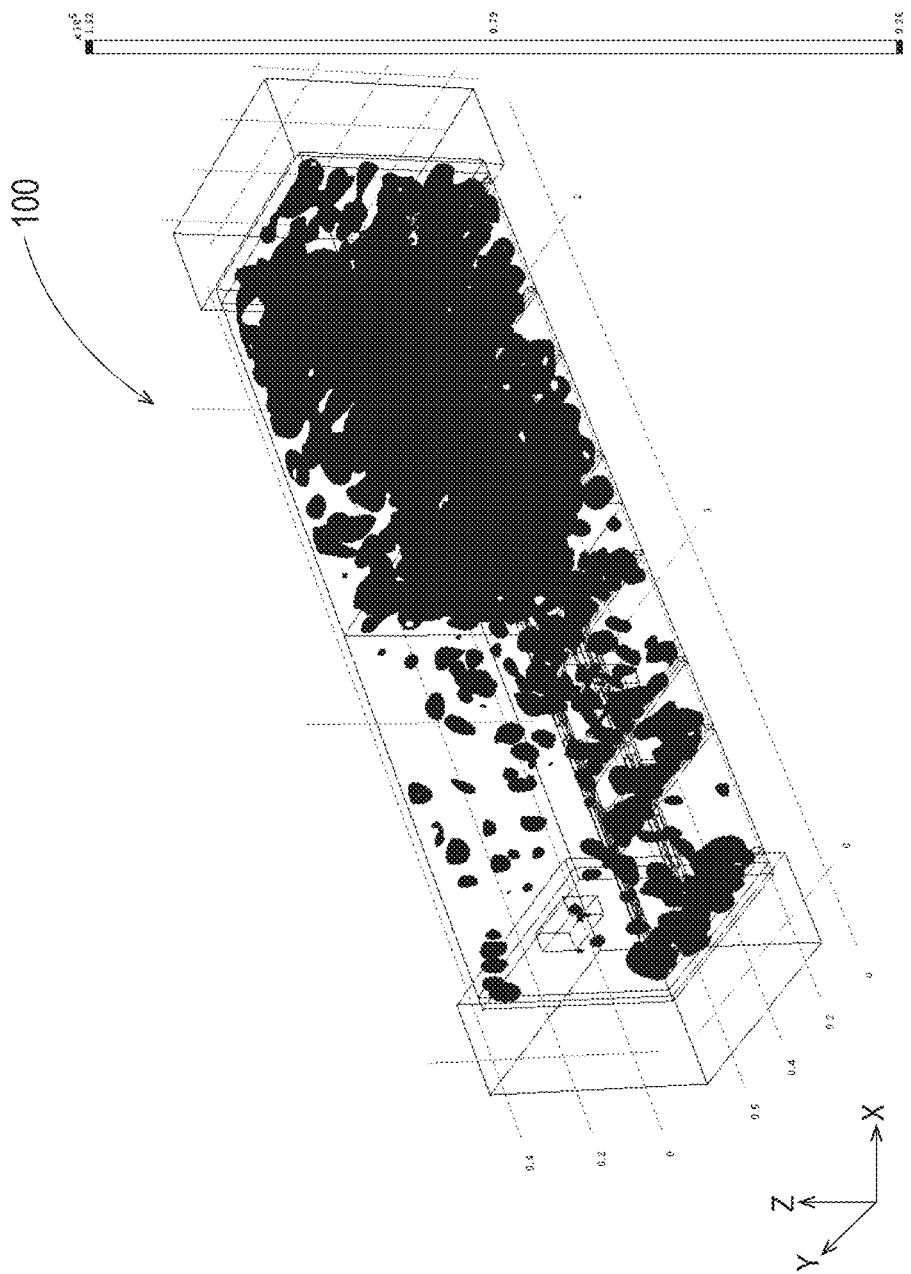
FIG. 22 is an exemplary E-field radiation density iso-surface plot of another exemplary elongate microwave oven having microwave transmitters disposed about the longitudinal axis of the elongate microwave oven and in an alternating orthogonal relationship relative to each other and where each successive microwave transmitter provides less microwave output than its predecessor as described herein.
Figure 23:
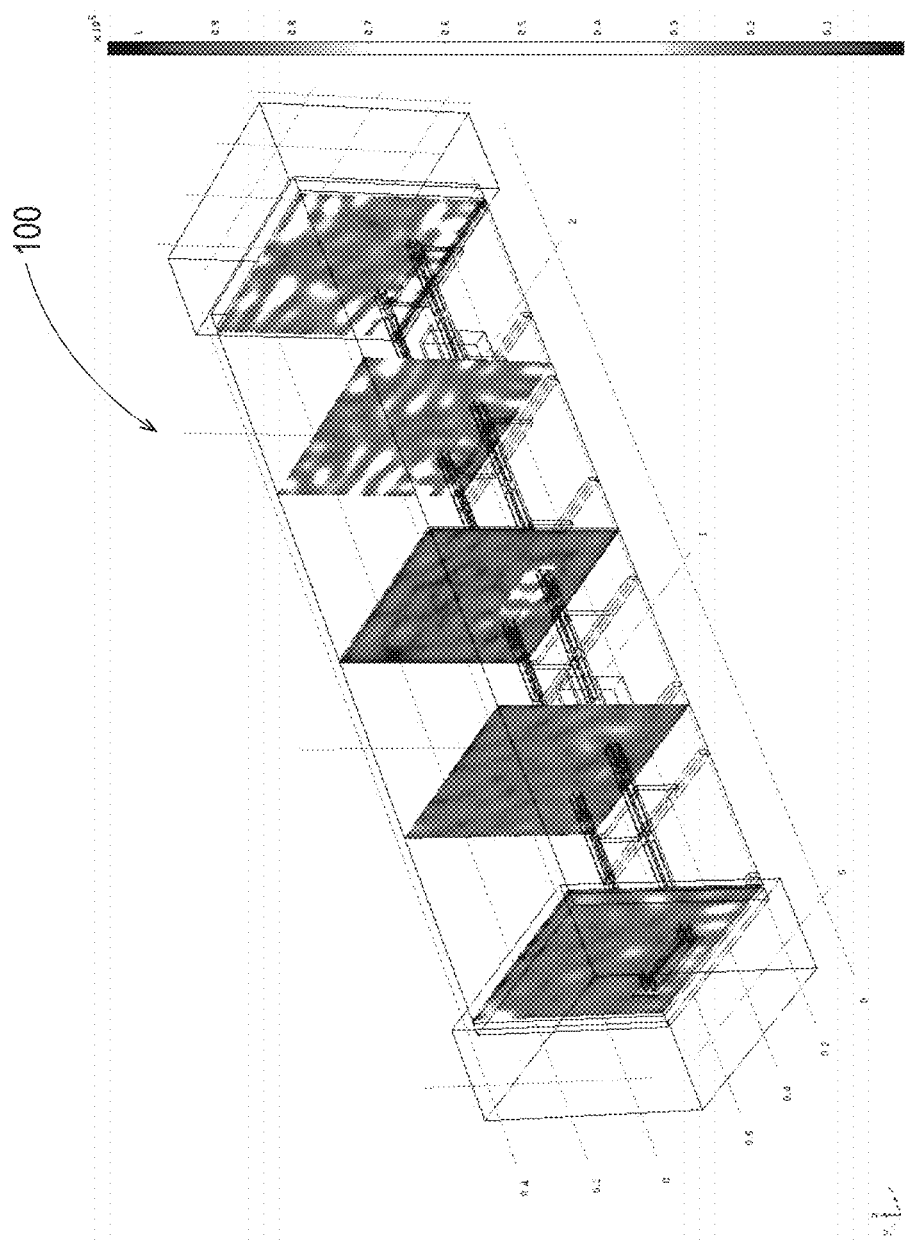
FIG. 23 is a plurality of cross-sectional views of an exemplary E-field radiation density plot in a plane formed by the y-z axis of the exemplary elongate microwave oven of FIG. 22; and, FIG. 24 is a cross-sectional view of an exemplary E-field radiation density plot in a plane formed by the x-y axis of the exemplary elongate microwave oven of FIG. 22.
Figure 24:
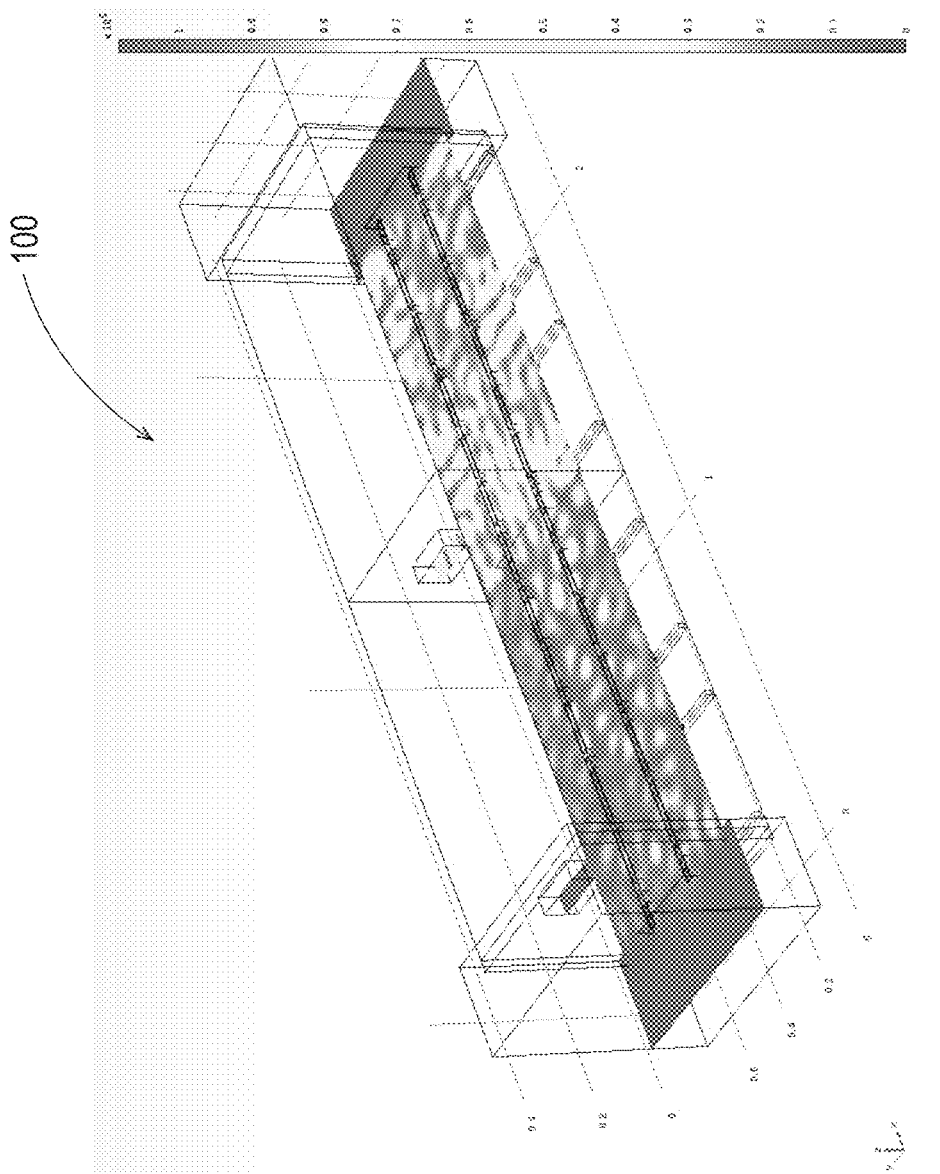

Referring to the exemplary embodiment provided in FIGS. 22-24, in some cases, it may be advantageous to not have a homogeneous power distribution within continuous feed elongate microwaving oven 100. This would be the case if thermal events became more common in the regular operation of the continuous feed elongate microwaving oven 100. That could include fires, equipment damage, or insufficient product shape stability. Without desiring to be bound by theory, it has been observed that thermal damage to a product is more likely to occur near the outlet of the continuous feed elongate microwaving oven 100. This could be caused by the already higher temperatures of the tampons disposed within this part of the continuous feed elongate microwaving oven 100. It is believed that the relatively colder tampons constantly entering the continuous feed elongate microwaving oven 100 near the inlet are much less likely to radiate or outwardly transfer heat to the surrounding area. It is believed that these relatively colder tampons entering the continuous feed elongate microwaving oven 100 and disposed near the inlet absorb heat from the applied microwave field making the inlet area of relatively colder tampons constantly entering the continuous feed elongate microwaving oven 100 near the inlet slightly more thermally stable.

In such a case, it could be beneficial to use a different power input (i.e., microwave transmitter output) scheme that provides a rapid rise in the temperature of the tampons when they first enter the continuous feed elongate microwaving oven 100, and reduce the heating rate towards the outlet of the continuous feed elongate microwaving oven 100. This can create a higher thermal history for the processed tampon. The thermal history is the amount of time at higher temperatures caused by the applied microwaves within the continuous feed elongate microwaving oven 100). Without being bound to any specific theory, this is believed to improve the shape stabilization of the tampon since the stabilization relationship is believed to be a function of time at an applied temperature.

As described supra, microwave transmitters can be disposed about a continuous feed elongate microwaving oven 100 in an alternating manner (e.g., first microwave transmitter disposed radially below the articles within continuous feed elongate microwaving oven 100, the next microwave transmitter orthogonal to the articles, etc.). If a particular continuous feed elongate microwaving oven 100 utilizes a two magnetron system, more microwave energy could be applied to the interior portion of continuous feed elongate microwaving oven 100 from the first microwave transmitter than from the second microwave transmitter. For example, this could be characterized by a power application of 2 units of energy near the inlet and 1 unit of energy near the outlet of the continuous feed elongate microwaving oven 100.

In an exemplary four magnetron system (e.g., first microwave transmitter disposed radially below the articles within continuous feed elongate microwaving oven 100, the next microwave transmitter orthogonal to the articles, third microwave transmitter disposed radially below (or above) the articles within continuous feed elongate microwaving oven 100, etc.), the power output from the series of microwave transmitters can be 'cascaded' so that each succeeding microwave transmitter provides less microwave energy than its immediate predecessor. By way of non-limiting example, a cascaded continuous feed elongate microwaving oven 100 system could have a first microwave transmitter provide 4 kW of microwave energy proximate to the inlet of continuous feed elongate microwaving oven 100, the second microwave transmitter provide 2.5 kW of microwave energy, a third microwave transmitter provide 1.5 kW of microwave energy, and the fourth microwave transmitter disposed adjacent the continuous feed elongate microwaving oven 100 outlet could provide 0 kW of microwave energy. Running the last magnetron with zero output power could make it unnecessary, but in an already installed system this profile could be implemented with no required physical equipment changes. As one of ordinary skill in the art can see, any arrangement of microwave radiation output by each respective microwave transmitter can be provided in order to provide the desired microwave energy profile for the process.

As shown in FIG. 22, such a cascaded microwave energy output can provide for a substantially uniform E-field density applied to the tampon pledget 50 and/or tampon 20 as it passes through the first chamber of continuous feed elongate microwaving oven 100. The second chamber of continuous feed elongate microwaving oven 100 can provide a similar substantially uniform E-field density, albeit at reduced E-field intensity.

Further, a review of the y-z cross-sectional E-field distribution (FIG. 23) does not identify any hot-spots (as would be shown by lighter/brighter color representations) within each respective chamber of continuous feed elongate microwaving oven 100. A review of the x-y cross-sectional E-field distribution (FIG. 24) also shows the presence of a substantially uniform E-field density in the plane of the tampon pledget 50 and/or tampon 20 within each chamber of continuous feed elongate microwaving oven 100 as it passes through the microwave oven 100. In short, a review of the various E-field density plots for a series of microwave transmitters distributed about continuous feed elongate microwaving oven 100 as described supra shows substantial uniformity in the desired E-field density and the absence of hot spots within each respective chamber of continuous feed elongate microwaving oven 100.

One of skill in the art will understand that microwaves are a type of high-frequency electromagnetic wave. The microwaves suitable for use with the present disclosure typically have a wavelength of around 12.23 cm and a frequency of 2.45 gigahertz (GHz). The electromagnetic waves produce oscillating magnetic and electric fields that excite molecules inside the field, therefore generating heat.

There are different factors that can contribute to a less-than-desirable microwave heating process by prior art systems. One factor is that different materials often have varying rates of energy absorption. This is due to the fact that materials having higher water content tend to absorb microwave energy with a higher efficiency, and materials having a lower water content absorb heat more slowly, causing uneven heating. This is due to the dipole that exists across a water molecule, which causes the negative and positive ends of the molecule to switch back and forth in the presence of the oscillating electromagnetic field.

Another reason for why microwaves of prior art microwave systems can heat a tampon pledget 50 and/or tampon 20 disposed within the continuous feed elongate microwaving oven 100 unevenly can come from the nature of the complicated oscillating pattern that takes place inside the continuous feed elongate microwaving oven 100.

The microwaves emitted from each respective microwave transmitting device of the series of microwave transmitting devices 120 are preferably directed toward the longitudinal axis 130 of the continuous feed elongate microwaving oven 100 or the conveyor belt 106 via each microwave transmitting device that is radiatingly coupled to the continuous feed elongate microwaving oven 100 that is usually a waveguide.

When tampon pledget 50 and/or tampon 20 is exposed to microwave radiation within the continuous feed elongate microwaving oven 100, the tampon pledget 50 and/or tampon 20 acts as a resonance cavity, trapping some of the electromagnetic field inside. The power transferred into the tampon pledget 50 and/or tampon 20, or the dissipated power is typically at least about 60%-80%, and preferably greater than 90%, of the total microwave energy emitted from each respective microwave transmitting device of the series of microwave transmitting devices 120. The rest of the microwave energy emitted from each respective microwave transmitting device of the series of microwave transmitting devices 120 is either reflected back through the respective microwave transmitting device of the series of microwave transmitting devices 120, lost out the openings 102/104, absorbed by the materials forming the microwave cavity, or outer sleeves 40.

Placing each respective microwave transmitting device of the series of microwave transmitting devices 120 orbitally about the longitudinal axis 130 or conveyor belt 106 of continuous feed elongate microwaving oven 100 so that the series of microwave transmitting devices 120 are not collectively elongate can lessen the problem of high intensity spots contributing to uneven heating and combustion. An exemplary uneven field distribution of microwave energy due to the orbital placement of a series of microwave transmitting devices 120 about the longitudinal axis 130 or conveyor belt 106 of continuous feed elongate microwaving oven 100 is shown in FIG. 14.

In conjunction with the curing energy from the series of microwave transmitting devices 120, the use of conventional forced hot air heat can be used advantageously. It can be beneficial to direct any forced hot air heat upward from directly below the conveyor belt 106. Advantageously, any hot air source can be provided to surround each respective microwave transmitting device of the series of microwave transmitting devices 120.

Next, tampon pledget 50, tampon 20, split cavity mold 34, and/or outer sleeve 40 are exposed to microwave energy until the shaped tampon 20 is self-sustained (i.e. properly heat-set). After the tampon 20 is self-sustained, the shaped tampon 20 may be removed by removing the split cavity mold 34 and/or outer sleeve 40 from the continuous feed elongate microwaving oven 100.

Next, if an outer sleeve 40 is used, the split cavity mold 34 may be ejected from the outer sleeve 40 through the second end 44 of the outer sleeve 40. Then, the split cavity mold 34 is split, that is at least partially separated or separated to the desired degree (e.g. partially opened) to aid the next step of tampon removal. Finally, the shaped tampon 20 is removed from the split cavity mold 34.

Any dimensions and/or values disclosed herein are not to be understood as being strictly limited to the exact dimensions and/or numerical values recited. Instead, unless otherwise specified, each such dimension and/or value is intended to mean both the recited dimension and/or value and a functionally equivalent range surrounding that dimension or value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An apparatus for applying a field of microwave energy for the processing of a material, the apparatus comprising:
    an elongate chamber having a proximal end, a distal end, and a longitudinal axis, said elongate chamber having a surface distributed about said longitudinal axis, said proximal end providing ingress for said material into said elongate chamber and said distal end providing egress of said material from said elongate chamber;
    a first microwave transmitting device radiatingly coupled to said elongate chamber at a first position proximate to said proximal end and oriented so that a first portion of said microwave energy is transmitted from said first microwave transmitting device and is directed toward said longitudinal axis;
    a second microwave transmitting device radiatingly coupled to said elongate chamber at a second position disposed between said first microwave transmitting device and said distal end and oriented so that a second portion of said microwave energy is transmitted from said second microwave transmitting device and is directed toward said longitudinal axis;
    a plurality of molds disposed within the elongate chamber, each of the plurality of molds comprising a mold cavity configured to receive a tampon pledget; and,
    wherein said second microwave transmitting device is coupled to said elongate chamber at a position relative to said longitudinal axis that ranges from about 30 degrees to about 150 degrees relative to said position of said first microwave transmitting device relative to said longitudinal axis.

2. The apparatus for applying a field of microwave energy for the processing of a material of claim 1 further comprising a third microwave transmitting device radiatingly coupled to said elongate chamber at a third position disposed between said second microwave transmitting device and said distal end and oriented so that a third portion of said microwave energy is transmitted from said third microwave transmitting device and is directed toward said longitudinal axis.

3. The apparatus for applying a field of microwave energy for the processing of a material of claim 2 further comprising a fourth microwave transmitting device radiatingly coupled to said elongate chamber at a fourth position disposed between said third microwave transmitting device and said distal end and oriented so that a fourth portion of said microwave energy is transmitted from said fourth microwave transmitting device and is directed toward said longitudinal axis.

4. The apparatus for applying a field of microwave energy for the processing of a material of claim 2 further wherein said elongate chamber further comprises a wall disposed internally therein, said wall subdividing said chamber into two elongate chamber portions, said first and second microwave transmitting device being disposed within a first elongate chamber portion of said two elongate chamber portions.

5. The apparatus for applying a field of microwave energy for the processing of a material of claim 1 wherein said first portion of said microwave energy transmitted from said first microwave transmitting device and directed toward said longitudinal axis comprises at least about 45% of said field of microwave energy.

6. The apparatus for applying a field of microwave energy for the processing of a material of claim 5 wherein said second portion of said microwave energy transmitted from said second microwave transmitting device and directed toward said longitudinal axis comprises at least about 35% of said field of microwave energy.

7. The apparatus for applying a field of microwave energy for the processing of a material of claim 1 wherein said first and second portions of said microwave energy are the same.

8. The apparatus for applying a field of microwave energy for the processing of a material of claim 1 further comprising a carrier mold for transporting said material from said proximal end to said distal end of said elongate chamber, said carrier mold being formed from a material substantially transparent to said microwave energy.

9. An apparatus for applying a substantially uniform field of microwave energy for the processing of a material, the apparatus comprising:
    an elongate chamber having a proximal end, a distal end, and a longitudinal axis, said elongate chamber having a surface distributed about said longitudinal axis, said proximal end providing ingress for said material into said elongate chamber and said distal end providing egress of said material from said elongate chamber;

a plurality of microwave transmitting devices each radiatingly coupled to said surface of said elongate chamber;

a first microwave transmitting device of said plurality of microwave transmitting devices being radiatingly coupled to said surface of said elongate chamber at a first position relative to said longitudinal axis and proximate to said proximal end, said first microwave transmitting device being oriented so that a first portion of said microwave energy is transmitted from said first microwave transmitting device and is directed toward said longitudinal axis; and, a second microwave transmitting device of said plurality of microwave transmitting devices being radiatingly coupled to said elongate chamber at a second position disposed orbitally about said longitudinal axis between said first microwave transmitting device and said distal end, said second microwave transmitting device being oriented so that a second portion of said microwave energy is transmitted from said second microwave transmitting device and is directed toward said longitudinal axis;

a plurality of molds disposed within the elongate chamber, each of the plurality of molds comprising a mold cavity configured to receive a tampon pledget.

10. The apparatus for applying a field of microwave energy for the processing of a material of claim 9 further comprising a third microwave transmitting device radiatingly coupled to said elongate chamber at a third position disposed between said second microwave transmitting device and said distal end and oriented so that a third portion of said microwave energy is transmitted from said third microwave transmitting device and is directed toward said longitudinal axis.

11. The apparatus for applying a field of microwave energy for the processing of a material of claim 10 further comprising a fourth microwave transmitting device radiatingly coupled to said elongate chamber at a fourth position disposed between said third microwave transmitting device and said distal end and oriented so that a fourth portion of said microwave energy is transmitted from said fourth microwave transmitting device and is directed toward said longitudinal axis.

12. The apparatus for applying a field of microwave energy for the processing of a material of claim 10 further wherein said elongate chamber further comprises a wall disposed internally therein, said wall subdividing said chamber into two elongate chamber portions, said first and second microwave transmitting device being disposed within a first elongate chamber portion of said two elongate chamber portions.

13. The apparatus for applying a field of microwave energy for the processing of a material of claim 9 wherein said first portion of said microwave energy transmitted from said first microwave transmitting device and directed toward said longitudinal axis comprises at least about 45% of said field of microwave energy.

14. The apparatus for applying a field of microwave energy for the processing of a material of claim 13 wherein said second portion of said microwave energy transmitted from said second microwave transmitting device and directed toward said longitudinal axis comprises at least about 35% of said field of microwave energy.

15. The apparatus for applying a field of microwave energy for the processing of a material of claim 9 wherein said first and second portions of said microwave energy are the same.

* * * * *